(12) United States Patent
Chapuis et al.

(10) Patent No.: US 6,333,503 B1
(45) Date of Patent: Dec. 25, 2001

(54) DEVICE AND PROCESS FOR NUCLEAR LOCATION BY WEIGHTED BARYCENTER CALCULATION USING PARALLEL-OPERATING DETECTORS, AND APPLICATION TO GAMMA CAMERAS

(75) Inventors: Alain Chapuis, St Martin-le-Vinoux; Claude Janin, Grenoble; Alain Noca, Gières, all of (FR)

(73) Assignee: Commissariat a l'Energie Atomique, Paris (FR)

(*) Notice: Subject to any disclaimer, the term of this patent is extended or adjusted under 35 U.S.C. 154(b) by 0 days.

(21) Appl. No.: 09/331,402
(22) PCT Filed: Dec. 18, 1997
(86) PCT No.: PCT/FR97/02349
§ 371 Date: Jul. 12, 1999
§ 102(e) Date: Jul. 12, 1999
(87) PCT Pub. No.: WO98/29762
PCT Pub. Date: Jul. 9, 1998

(30) Foreign Application Priority Data

Dec. 31, 1996 (FR) .................................................. 96 16294

(51) Int. Cl.$^7$ .................................................. G01T 1/208
(52) U.S. Cl. .................................................. 250/369; 250/366
(58) Field of Search .................................................. 250/369, 370.1, 250/370.11, 366, 363.02, 363.03

(56) References Cited

U.S. PATENT DOCUMENTS 3,011,057  11/1961  Anger .
4,672,542 *  6/1987  Roux et al. ............................. 378/34
4,900,931 *  2/1990  Tournier et al. ...................... 250/369
5,185,529 *  2/1993  Smith et al. ........................... 250/369
5,371,362  12/1994  Mestais et al. .
5,444,253 *  8/1995  Berlad .................................. 250/369
5,504,334 *  4/1996  Jensen et al. ......................... 250/369
5,508,524 *  4/1996  Goldberg et al. .................... 250/369
5,576,547 * 11/1996  Ferreira et al. ...................... 250/369
5,952,662 *  9/1999  McDaniel ............................. 250/369
6,057,551 *  5/2000  Tararine ........................... 250/363.03

FOREIGN PATENT DOCUMENTS 2 669 439    5/1992   (FR) .

* cited by examiner

Primary Examiner—Constantine Hannaher
Assistant Examiner—Albert Gagliardi
(74) Attorney, Agent, or Firm—Burns Doane Swecker & Mathis LLP

(57) ABSTRACT

The invention relates to a process and a device for determining the position $P_0$ of an event with respect to a set of N photodetectors, inducing a signal in the N photodetectors. This process comprises the following steps:

a) digitize the signal output by each photodetector; calculate the energy of the signal output by each photodetector, b) calculate the contribution of the column to the total energy, to the X value of the center of gravity of the event and to the Y value of the center of gravity of the event, for each column, c) determine the total energy induced by the event and the coordinates of the center of gravity of the event with respect to the N photodetectors.

37 Claims, 14 Drawing Sheets

DEVICE AND PROCESS FOR NUCLEAR LOCATION BY WEIGHTED BARYCENTER CALCULATION USING PARALLEL-OPERATING DETECTORS, AND APPLICATION TO GAMMA CAMERAS

DESCRIPTION

Technical domain

This invention relates to a device for determining the position of an event inducing a signal in photodetectors, for example this position being identified with respect to the set of photodetectors. This type of position can be identified by the center of gravity of the event in a coordinate system relative to the photodetectors.

The invention is particularly applicable to determining the position of an event starting from signals output by photo-multipliers used in a gamma-camera, the position being identified with respect to the photo-multipliers themselves. A gamma-camera is a camera that is sensitive to gamma ($\gamma$) radiation. This type of camera is used particularly for medical imagery purposes.

STATE OF PRIOR ART

At the present time, most gamma-cameras used in nuclear medicine operate using the principle of Anger type cameras. Document U.S. Pat. No. 3,011,057 provides further information about this subject.

Gamma-cameras have the specific feature that they display the distribution of molecules marked by a radioactive isotope previously injected into the patient, within an organ.

The structure and operation of a known gamma-camera are described and summarized below with reference to the attached FIGS. 1, 2A and 2B.

FIG. 1 shows a detection head 10 of a gamma-camera placed facing an organ 12 containing molecules marked by a radioactive isotope.

The detection head 10 comprises a collimator 20, a scintillator crystal 22, a light guide 24 and several photo-multiplier tubes 26 placed adjacent to each other so as to cover one surface of the light guide 24. For example, the scintillator may be an NaI (Tl) crystal.

The function of the collimator 20 is to select the radiation which reaches the detection head at an approximately normal incidence, among all the gamma radiation 30 emitted by organ 12. The selective nature of the collimator can increase the resolution and the sharpness of the image produced. However, the resolution is increased at the expense of sensitivity. For example, only one photon among about 10 000 $\gamma$ photons emitted by organ 12, is actually detected.

The $\gamma$ photons that passed through the collimator arrive at the scintillator crystal 22, where almost all $\gamma$ photons are converted into several light photons. In the rest of this text, each interaction of a gamma photon with the crystal causing a scintillation is called an event.

Photo-multipliers 26 are designed to emit an electric pulse proportional to the number of light photons received from the scintillator for each event.

In order for a scintillation event to be more precisely positioned, photo-multipliers 26 are not directly fixed to the scintillator crystal 22 but are separated from it by the light guide 24.

Photo-multipliers emit a signal, the amplitude of which is proportional to the total quantity of light produced in the scintillator by gamma radiation, in other words proportional to its energy. However, the individual signal from each photo-multiplier also depends on the distance that separates it from the point 30 at which the gamma radiation interacts with the scintillator material. Each photo-multiplier outputs a current pulse proportional to the light flux that it received. In the example in FIG. 1, small graphs A, B and C show that photo-multipliers 26a, 26b and 26c located at different distances from an interaction point 30 output signals with different amplitudes.

The position of the interaction point 30 of a gamma photon is calculated in the gamma-camera starting from signals originating from the set of photo-multipliers by taking a center of gravity weighting of the contributions of each photo-multiplier.

The principle of center of gravity weighting as used in Anger type cameras can be explained more clearly with reference to attached FIGS. 2A and 2B.

FIG. 2A shows the electric wiring of a gamma-camera detection head 10, that connects this camera to an image generation unit. The detection head comprises several photo-multipliers 26.

As shown in FIG. 2B, each photo-multiplier 26 in the detection head is associated with four resistances denoted $RX^-$, $RX^+$, $RY^-$ and $RY^+$. The values of these resistances are specific to each photo-multiplier and depend on the position of the photo-multiplier in the detection head 10.

Resistances $RX^-$, $RX^+$, $RY^-$ and $RY^+$ in each photo-multiplier are connected to the output 50 of the said photo-multiplier, represented in FIG. 2B by a current generator symbol. They are also connected to common collecting rows denoted $LX^-$, $LX^+$, $LY^-$ and $LY^+$ respectively in FIG. 2A.

Rows $LX^-$, $LX^+$, $LY^-$ and $LY^+$ are in turn connected to analog integrators $52X^-$, $52X^+$, $52Y^-$ and $52Y^+$ respectively, and through these integrators to analog/digital converters $54X^-$, $54X^+$, $54Y^-$ and $54Y^+$ respectively. The output from converters $54X^-$, $54X^+$, $54Y^-$ and $54Y^+$ is directed towards a digital operator 56. Rows $LX^-$, $LX^+$, $LY^-$ and $LY^+$ are also connected to a common channel, called the energy channel. This channel also comprises an integrator 57 and an analog/digital converter 58, and its output is also directed towards operator 56.

The device in FIG. 2 is used to calculate the position of the interaction according to the following equations (U.S. Pat. No. 4,672,542):

$$X = \frac{X^+ - X^-}{X^+ + X^-}$$

and $$Y = \frac{Y^+ - Y^-}{Y^+ + Y^-}$$

in which X and Y are the coordinates along two orthogonal directions of the position of the interaction on the crystal, and in which $X^+$, $X^-$, $Y^+$, $Y^-$ represent the weighted signals output by integrators $52X^+$, $52X^-$, $52Y^+$, $52Y^-$ respectively.

The values of X and Y, and the total energy E of the gamma ray that interacted with the crystal, are established by the digital operator 56. These values are then used to generate an image, for example as described in document FR-2 669 439.

The calculation of the interaction position is affected by an uncertainty related to Poisson statistical fluctuations in the number of light photons and the number of photoelectrons produced for each event, in other words for each detected gamma photon. The standard deviation of the fluctuation reduces when the number of photons or photo-electrons increases. Due to this phenomenon, light should be collected as carefully as possible. The intrinsic spatial resolution of the camera is characterized by the width at the mid-height of the distribution of positions calculated for the same collimated point source placed on the scintillator crystal.

The resolution for gamma rays with an energy of 140 keV is usually of the order of 3 to 4 mm.

The energy of a detected gamma photon is calculated by taking the sum of the contributions of all photo-multipliers that received light. It is also affected by a statistical fluctuation. The energy resolution of the camera is characterized by the ratio of the width at the mid-height of the distribution of calculated energies, to the average value of the distribution, for the same source.

The energy resolution is usually of the order of 9 to 11% for gamma rays with an energy of 140 keV.

Finally, an Anger type gamma-camera has the advantage that it enables real time calculation of the center of gravity of photo-multiplier signals with very simple means.

The system described above has a limited number of components. Furthermore, the resistances used to inject the photo-multiplier signal in collecting rows are not very expensive.

However, this type of camera also has a major disadvantage, which is a low count rate. The count rate is the number of events, in other words the number of interactions between a γ photon and the scintillator, that the camera is capable of processing per unit time.

One of the limitations in the count rate is particularly due to the fact that the camera is incapable of processing two events that take place approximately simultaneously at distinct points in the scintillator crystal.

Simultaneous but geometrically distinct events create electrical signals that are stacked in the $LX^-$, $LX^+$, $LY^-$ and $LY^+$ collecting rows and which can no longer be distinguished. These events are also "lost" for the formation of an image.

The limitation in the count rate is not an excessive constraint in traditional medical imagery techniques. As mentioned above, the collimator stops a very large number of gamma rays and only a small number of events are actually detected.

However, gamma cameras are also used in two other medical imagery techniques in which the limitation of the count rate is an unacceptable constraint.

These techniques are called "correction of transmission attenuation" and "coincident PET (Positron Emission Tomography)".

The correction of transmission attenuation technique consists of taking account of the attenuation specific to the tissue of the patient surrounding the examined organ, during the formation of a medical image. In order to determine this attenuation, the transmission of gamma radiation through the patient's body to a gamma-camera is measured. This is done by putting the patient between a highly active external source and the gamma-camera detection head. Thus when measuring the transmitted radiation, a large number of events take place in the scintillator crystal. The large number of events per unit time also increase the probability of having several almost simultaneous events. A conventional Anger type camera is then not suitable.

The PET technique consists of injecting an element such as $F^-$ into the patient, capable of emitting positrons. The neutralization of a positron and an electron releases two γ photons emitted in opposite directions with an energy of 511 keV. The PET imagery technique makes use of this physical phenomenon, by using a gamma-camera with at least two detection heads placed on each side of the patient. The detection heads used are not equipped with a collimator. Electronic information processing, called coincidence processing, selects events that occur at the same time, and thus calculates the trajectory of gamma photons.

Therefore, detection heads are subjected to high gamma radiation fluxes. The count rate of conventional Anger type gamma-cameras is usually too limited for this type of application.

For guidance, an Anger type gamma-camera can operate normally with a detection of $1 \times 10^5$ events per second, although in PET imagery at least $1 \times 10^6$ events per second are necessary for normal operation.

Another limitation of Anger type gamma-cameras described above, is due to the fact that the calculation of the center of gravity of an event is fixed by the construction of the detection head and cannot be changed, and particularly by the choice of the resistances $RX^-$, $RX^+$, $RY^-$, $RY^+$, for each photo-multiplier. Similarly, the energy calculation is fixed by wiring photo-multipliers on a common channel (energy channel).

Therefore, devices and processes need to be developed to enable use of gamma-cameras with a high count rate.

DESCRIPTION OF THE INVENTION

The purpose of the invention is a process for determination of the position $P_0$ of an event with respect to a set of N photodetectors, this event inducing a signal in the N photodetectors, and this process comprising the following steps:

a) a step in which the signal output by each photodetector is digitized, and a value $N_{i,j}$ representing the energy of the signal output by each photodetector is calculated, b) a step in which the following are determined for each column i:

the contribution of the column to the total energy induced by the event in the set of photodetectors, the contribution of the column to the X value of the center of gravity of the event, the contribution of the column to the Y value of the center of gravity of the event c) a step in which the following are determined:

the total energy induced by the event in the set of photodetectors, the coordinates of the center of gravity $(X_0, Y_0)$ of the event with respect to the N photodetectors.

This type of process is capable of processing digitized data, and can produce a position signal $P_0$ or, more precisely a pair of coordinates of the center of gravity $(X_0, Y_0)$ of the event with respect to the set of N photodetectors.

This process can be used for the operation of gamma-cameras with a high count rate, which is very advantageous in the case of "correction of transmission attenuation" and "coincident PET" measurements.

The high count rate is achieved without restricting the number of photodetectors read. This is due to the parallelism used and the large amount of pipelining, in other words the sequence of single operations.

The process according to the invention as described above, can accelerate the calculation of the center of gravity of digitized contributions of photodetectors by carrying out this calculation in parallel.

A process in which the digitized data corresponding to each photodetector would be stored and then read would not be sufficient to make the calculation of the center of gravity of the event compatible with the high count rate.

Photodetectors may be read in serial mode or in parallel mode:

serial mode: photodetectors are read one after the other on a serial bus;

parallel mode: several photodetectors in the same row are read at the same time on column buses.

For example, if it is assumed that 100 nsec is necessary (non-limitative value giving an order of magnitude), 3 μsec would be necessary to read 30 photodetectors which would give a maximum count rate of 330 000 events/second in serial mode. If six 100 nsec read steps are carried out on 6 column buses in parallel mode, 36 photodetectors will have been read in 600nsec corresponding to a count rate exceeding 1.6 million events/sec. This also requires that use can be made of this throughput, so that the calculation does not impose a limit on the count rate. This is possible using the process according to the invention.

Obviously, within the framework of the invention, columns can be replaced by rows and the calculation principle will remain the same.

It would be possible to carry out a preliminary step to detect the presumed position of an event. In this case, a subset of $N_1$ photodetectors among the N photodetectors could be delimited around this presumed position, only the signals from these $N_1$ photodetectors being used to carry out steps b and c above.

According to another aspect, after the coordinates of the center of gravity ($X_0$, $Y_0$) of the event have been determined with respect to the N photodetectors, the following steps can be carried out:

d) determine the distance $D_{i,j}$ between $P_0$ and each photodetector used in steps b) and c), e) weighting the signal $N_{i,j}$ output by each photodetector considered, to obtain a weighted signal value $N'_{i,j} = K*N_{i,j}$ where K is a function of $d_{i,j}$.

It is then possible to perform the following:

b') a step in which the following are determined using the values of the weighted signal, $N'_{i,j}$, for each column i:
the contribution of the column to the total energy induced by the event in the set of photodetectors,
the contribution of the column to the X value of the center of gravity of the event,
the contribution of the column to the Y value of the center of gravity of the event;

c') a step in which the following are determined using the values of the weighted signal, $N'_{i,j}$:
the total energy induced by the event in the set of photodetectors,
the new coordinates of the center of gravity ($X'_0$, $Y'_0$) of the event with respect to the N photodetectors.

Thus, the accuracy of the value of the position obtained is improved.

According to another aspect, after the coordinates of the center of gravity $P_0$ ($X_0$, $Y_0$) of the event with respect to the N photodetectors have been determined, the following steps can be carried out:

d') determine the distance $d_{i,j}$ between $P_0$ and each photodetector considered in steps b) and c), f) compare with a value D, for each value of $d_{i,j}$, g) determine the value $N_{i,j}*PD$, where PD=0 if $d_{i,j}>D$ and PD≠0 if $d_{i,j} \leq D$, for each photodetector.

A new value of the total energy can then be determined as a function of the values $N_{i,j}*PD$.

The accuracy of the energy is then improved.

Another purpose of the invention is a device for implementing the process described above.

A device of this type comprises:

a) means of digitizing a signal output by each photodetector, and for calculating a value $N_{i,j}$ representative of the energy of the signal output by each photodetector, b) means of determining for each column i:
the contribution of the column to the total energy induced by the event in the set of photodetectors,
the contribution of the column to the X value of the center of gravity of the event,
the contribution of the column to the Y value of the center of gravity of the event, c) means of determining:
the total energy induced by the event in the set of photodetectors,
the coordinates of the center of gravity of the event with respect to the N photodetectors.

BRIEF DESCRIPTION OF THE FIGURES

In any case, the characteristics and advantages of the invention will become clearer after reading the following description. This description applies to example embodiments given for explanatory purposes and in no way restrictive, with reference to the attached drawings, in which.

DETAILED DESCRIPTION OF EMBODIMENTS OF THE INVENTION

The invention will be described in a detailed manner for the photo-multipliers in a gamma-camera. However, this description is equally valid for any photodetectors, not necessarily forming part of a gamma-camera.

Figure 1:
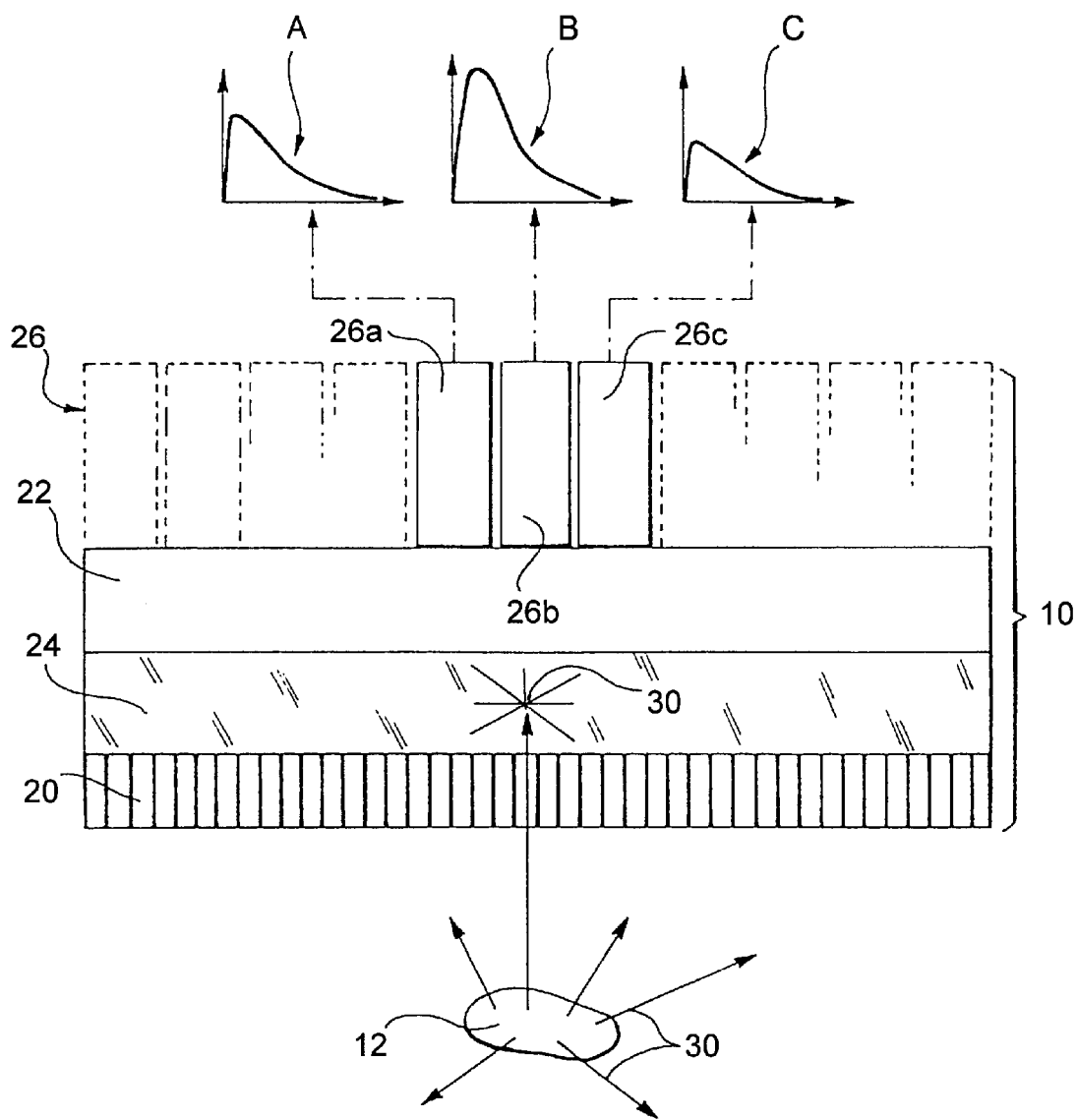
FIG. 1, described above, is a diagrammatic section through a detection head of a known type of Anger camera.
Figure 2B:
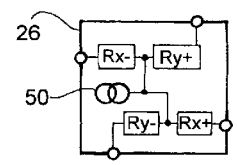
FIG. 2 described above, diagrammatically shows a device for collecting and encoding signals originating from photo-multipliers in the detection head according to FIG. 1.
Figure 2A:
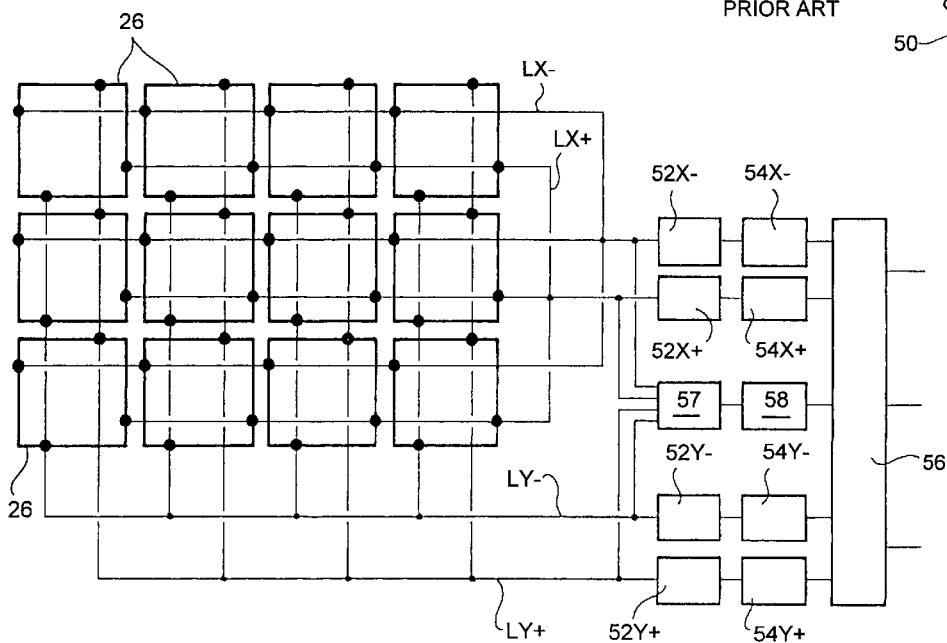
Figure 3:
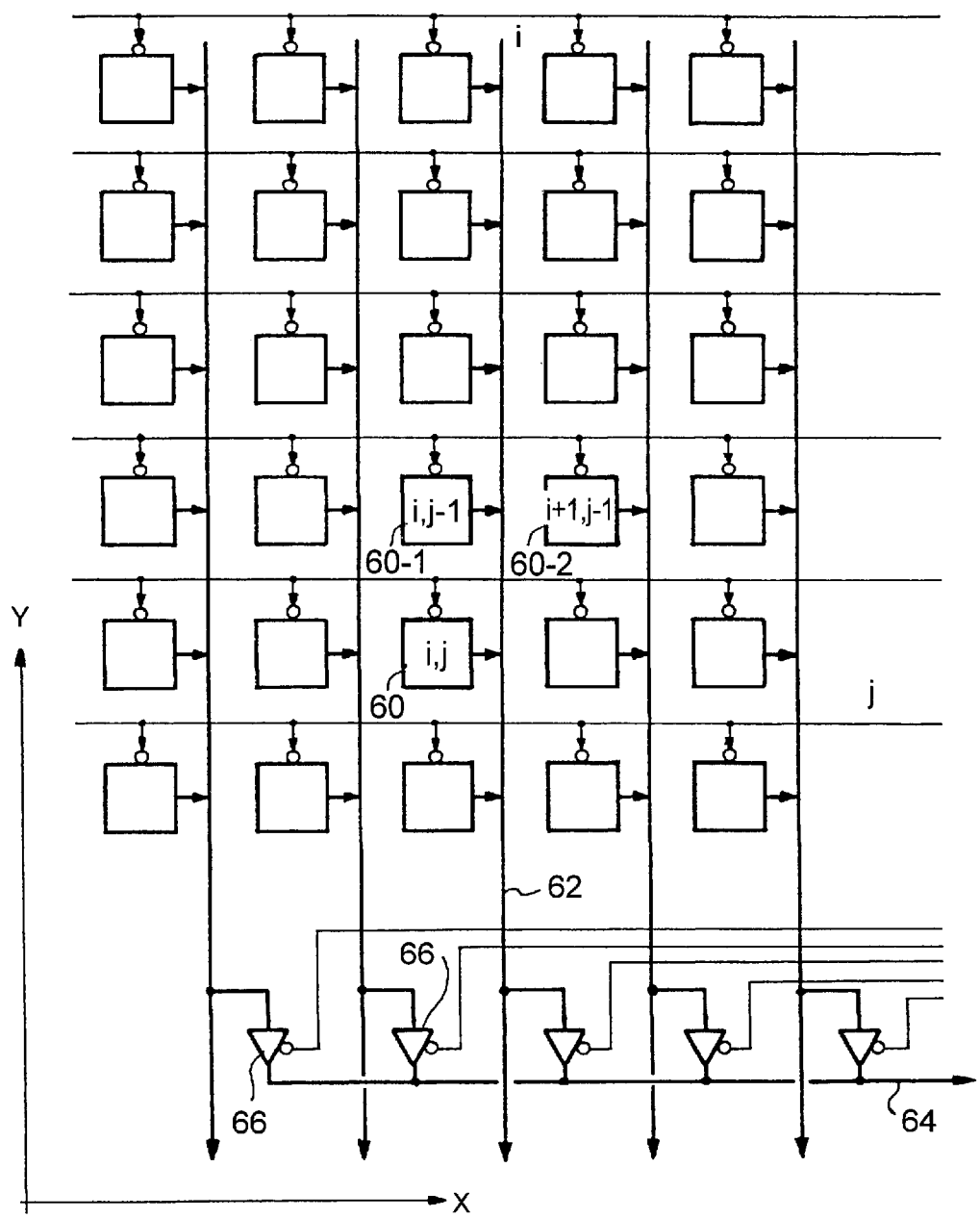
FIG. 3 shows the interconnection of a set of photodetectors.

FIG. 3 shows a set of photo-multipliers 60, 60-1, 60-2, etc., making up a gamma-camera head. Each photo-multiplier is identified by its position (i,j) in the set of photo-multipliers. More precisely, the coordinates along the two axes X, Y of the center of photo-multiplier i, j, are denoted $Xc_{i,j}$ and $YC_{i,j}$.

Figure 13:
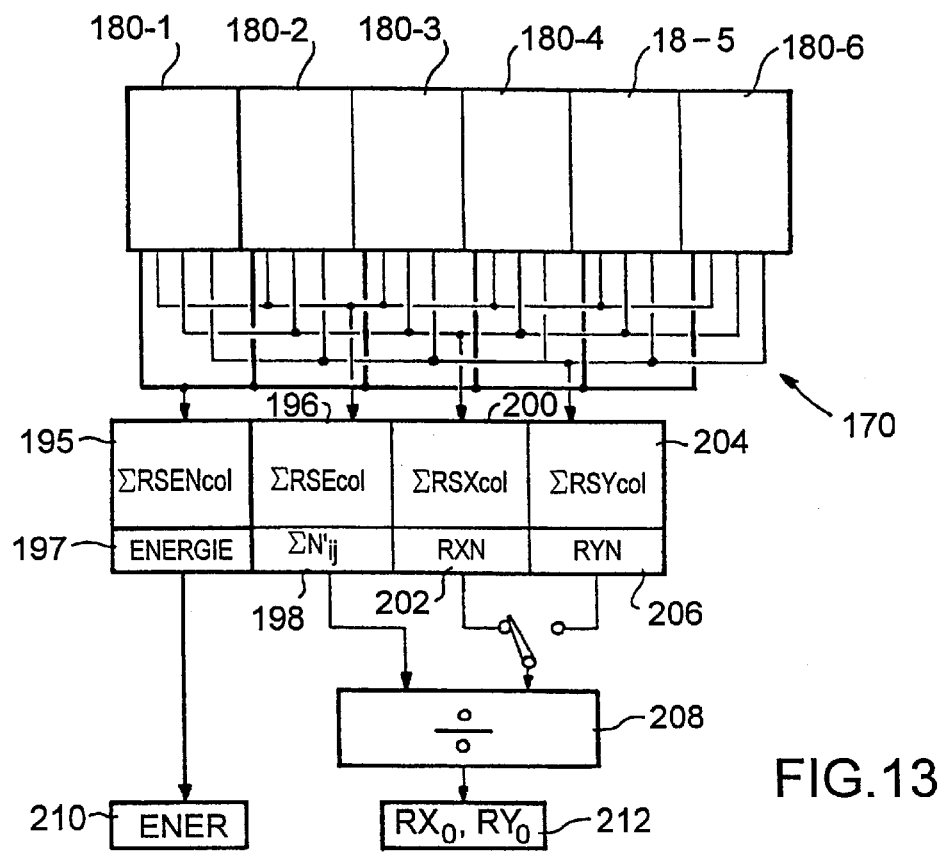
FIG. 13 shows the structure of a calculation system for another embodiment of the invention.

The signal output from each photo-multiplier is digitized and processed individually (integration, corrections, etc.). Each photo-multiplier has a storage register level that is used to memorize the contribution of each photo-multiplier when an event is detected. These aspects will be described later in relation to FIGS. 13–14B.

The photo-multipliers network is organized in rows and columns, and all outputs from photo-multipliers storage registers in the same column are connected to a bus 62 (column bus). Column buses may be collected in one serial bus 64.

Figure 4:
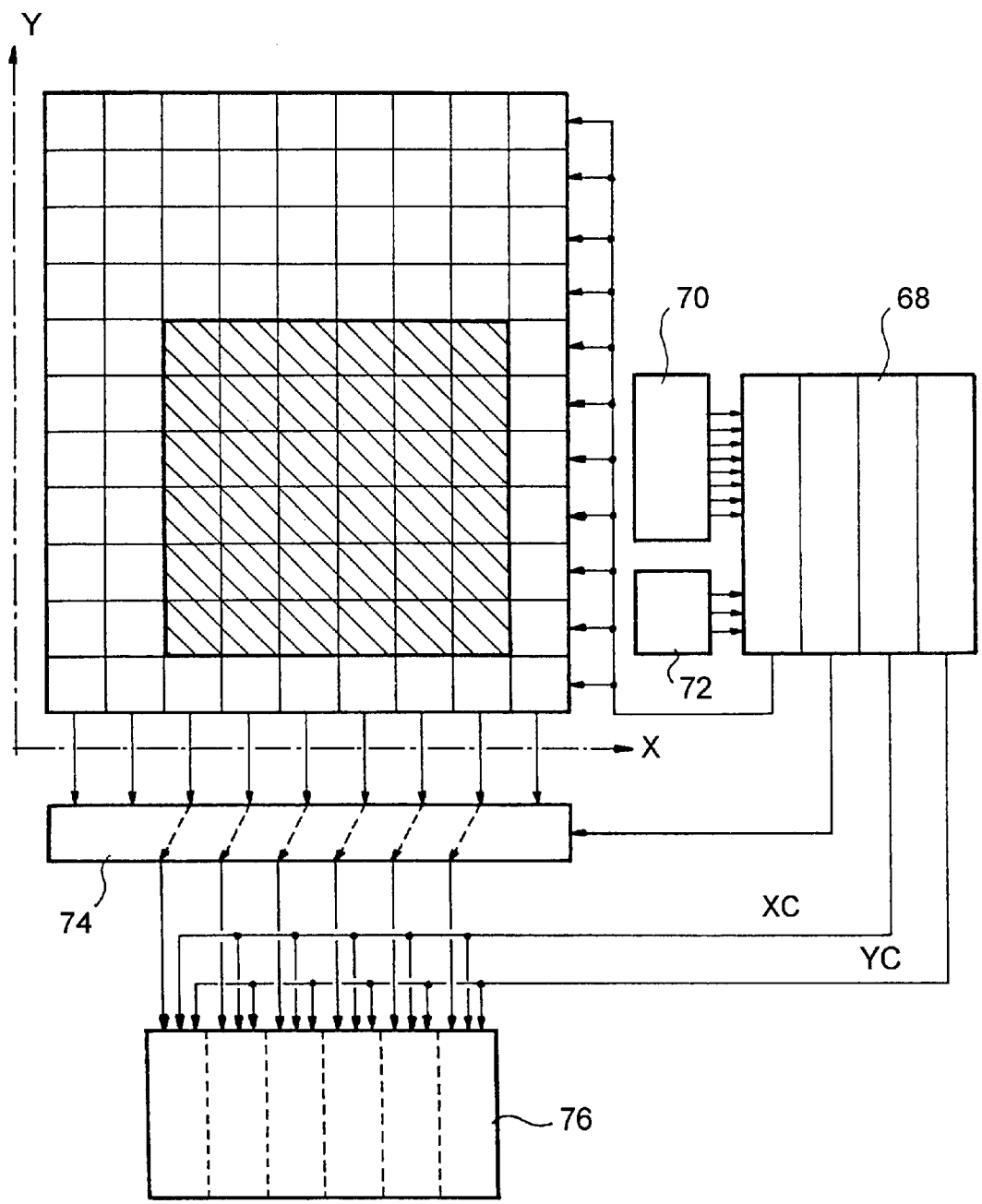
FIG. 4 shows a device for reading a set of photodetectors, for an embodiment of the invention.

Means 66 are used to select each column independently of the other columns. For example, these means 66 may be controlled by a read sequencer 68 (FIG. 4).

When the photo-multipliers network is not too large, the set of photo-multipliers can be used.

However when the photo-multipliers network is large (for example between 50 and 100 photo-multipliers), an uncorrected position of the event is determined first, for example using a method that will be described later with relation to FIG. 15.

The fact of knowing the interaction area of the event already limits the number of photo-multipliers that have to be used to calculate the position and energy of the interaction. In fact, usually only the two photo-multiplier rings that surround the photo-multiplier at which the interaction occurs contain any significant information.

Since the accuracy of the presumed position is inadequate, it is often necessary to read a larger area than is strictly necessary (for example often up to 25 or 30 reads per event). The time necessary to read storage registers to process an event is a compulsory operation that has a direct influence on the count rate of the machine (number of events processed per second).

FIG. 4 more precisely illustrates a device for embodiment of the invention.

A read sequencer 68 reads the contents of the storage register for each photo-multiplier. Let $N_{i,j}$ be the contents of the storage register for the photo-multiplier for column i and row j. $N_{i,j}$ may actually represent a digital integral of the signal output by the photo-multiplier i, j in response to an event.

Means 70 determine a presumed or uncorrected position of the event. These means will be described later in more detail (FIG. 15).

The read sequencer 68 controls addressing of columns by a multiplexer 74. The contribution of each column to the total energy, to the X component of the center of gravity (XC) and the Y component of the center of gravity (YC) is transferred to a calculation system 76 either by addressing of the columns through the multiplexer, or directly through the calculation sequencer 68.

The number of columns and rows used around each presumed position is imposed by the inaccuracy of the determination. In FIG. 4, 36 (6×6) photo-multipliers are used. In general, for a field of N photo-multipliers, it will be necessary to use $N_1$ photo-multipliers ($N_1$<N) depending on the required accuracy; in FIG. 4, N=11×9 and $N_1$=6×6.

Consequently, there is a presumed position (PP) corresponding to each event, and a set of $N_1$ (36) photo-multipliers located on 6 successive rows and 6 successive columns is made to correspond to each presumed position, such that all photo-multipliers in which information is stored are selected. The read sequencer 68 supplies the following at each read step (every 100 nsec) as a function of the presumed position:

commands necessary to the multiplexer 74 so that it can orient the column buses to be read towards the calculation device 76, row selection signals so as to present the storage registers controlled by row n on column buses for the first read time, and then storage registers controlled by row n+1 for the second read time, and so on until reading row n+5 for the sixth read time, the coordinates XC and YC of the centers of the photo-multipliers presented on the column buses.

The sequencer may be made in the form of an EPROM. A memory page corresponds to each presumed position, and the commands and values necessary for the calculation are described in this memory page. This page is read row by row using a counter 72 that activates the low addresses of the EPROMs.

The energy and/or the position, in X and Y, of an event can be summarized as follows:

a) The energy of the event is the sum of the contributions of all photo-multipliers that surround the presumed position:

$$E = \sum_{i,j} N_{i,j}$$

This expression can also be written:

$$E = \sum_{i} \left| \sum_{j} N_{i,j} \right|, \text{ where } \sum_{j} N_{i,j} \text{ is the sum of the}$$

contribution of the six photo-multipliers in column i, the energy E being the sum of the energies obtained on the six columns.

b) The position of the event is calculated using the center of gravity method:

$$\bullet X = \sum_{i,j} (XC_{i,j} * N_{i,j}) \bigg/ \sum_{i,j} N_{i,j}, \text{ where } XC_{i,j} \text{ is the } X$$

coordinate of the center of the photo-multiplier located on column i and row j, $$\bullet Y = \sum_{i,j} (YC_{i,j} * N_{i,j}) \bigg/ \sum_{i,j} N_{i,j}, \text{ where } YC_{i,j} \text{ is the } Y$$

coordinate of the center of the photo-multiplier located on column i and row j,

As above, we can also write:

$$\bullet X = \sum_{i} \left| \sum_{j} (XC_{i,j} * N_{i,j}) \right| \bigg/ \sum_{i,j} N_{i,j}, \text{ where } \sum_{j} (XC_{i,j} * N_{i,j})$$

is the contribution to the X coordinate of the center of gravity of the 6 photo-multipliers in column i, $$\bullet \, Y = \sum_i \left| \sum_j (YC_{i,j} * N_{i,j}) \right| / \sum_{i,j} N_{i,j}, \text{ where } \sum_j (YC_{i,j} * N_{i,j})$$

is the contribution to the Y coordinate of the center of gravity of the 6 photo-multipliers in column i.

If a set of $N_1$ photo-multipliers is considered instead of 6×6 photo-multipliers only, then the above formulas are still applicable, the sums being applied to the corresponding rows and columns.

The structure of the calculation device 76 will now be described more precisely in relation to FIGS. 5 and 6.

Figure 5:
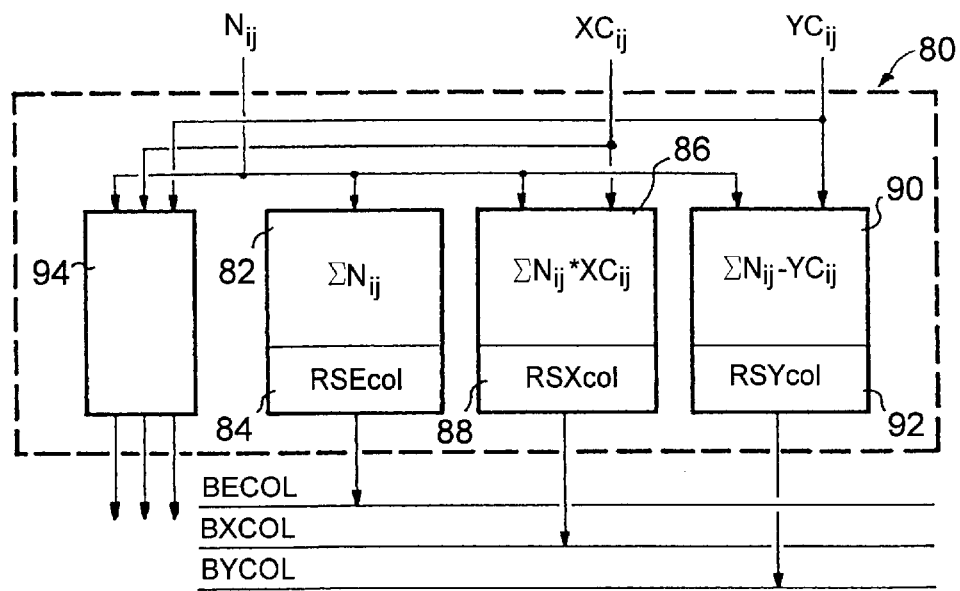
FIG. 5 shows the structure of a column operator for an embodiment of the invention.
Figure 6:
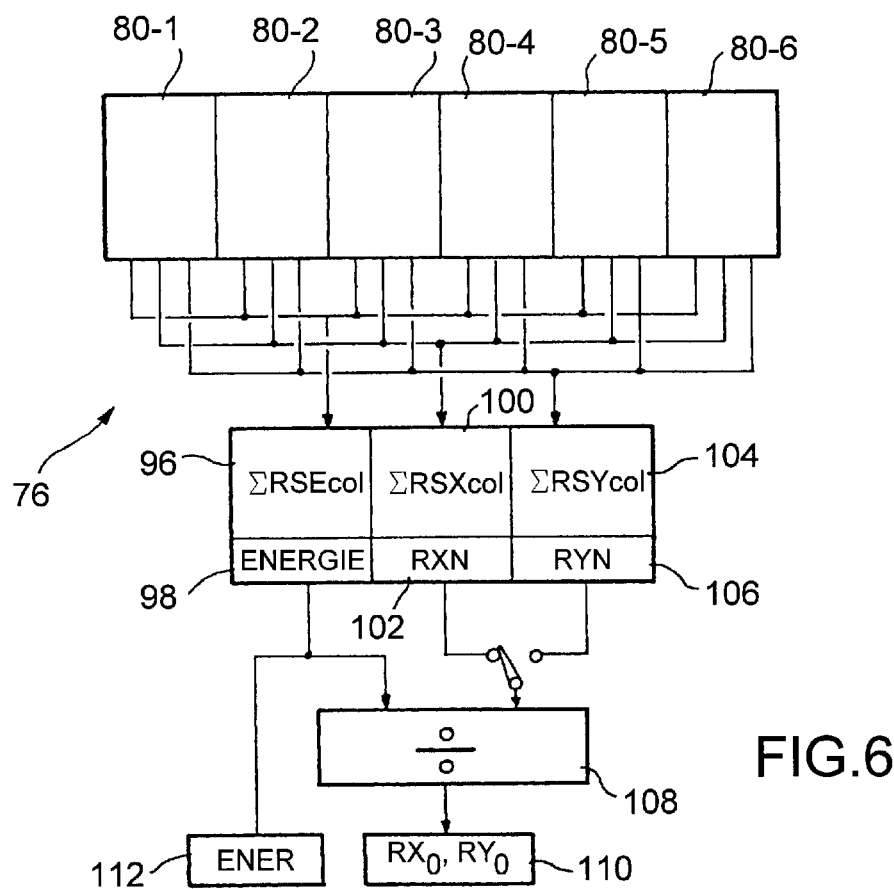
FIG. 6 shows the structure of a calculation system for an embodiment of the invention.

FIG. 5 shows means 80 associated with each column and subsequently denoted the column operator.

In addition to the values $N_{i,j}$ of column photo-multipliers, this device also receives the coordinates $XC_{i,j}$ and $YC_{i,j}$ of the centers of the corresponding photo-multipliers, for example output by the read sequencer 68. The X coordinates are not necessarily identical for the same column, since they must take account of the real position of the photo-multiplier within the field of gamma-camera. The same is true for the Y coordinates. In the example given, each output from the column bus is connected to the input of a column operator 80.

Each column operator 80 performs three operations, preferably in parallel.

A first operation consists of calculating the contribution of the column to the energy. For example, after being initialized at the beginning of the sequence, an accumulator 82 takes the sum of the values $N_{i,j}$ of the 6 photo-multipliers in the column and stores the result in a register 84 (RSEcol). The outputs from the six registers (RSEcol1 to RSEcol6) are grouped on a common bus BECOL.

A second operation consists of calculating the contribution of the column to the X value of the center of gravity. For example, after being initialized at the beginning of the sequence, a multiplier-accumulator 86 takes the sum of the contributions to the X value of the center of gravity of the 6 photo-multipliers in the column, and stores the result in a register 88 (RSXcol). The outputs from the six registers (RSXcol1 to RSXcol6) are grouped on a common bus BXCOL.

A third operation consists of calculating the contribution of the column to the Y value of the center of gravity. For example, after being initialized, a second multiplier-accumulator 90 takes the sum of the contributions to the Y value of the center of gravity of the 6 photo-multipliers in the column, and stores the result in a register 92 (RSYcol). The outputs from the six registers (RSYcol1 to RSYcol6) are grouped on a common bus BYCOL.

At the end of the 6 read times, the 6 column operators that have completed their work become available for another read since the results of the first read are stored.

In parallel to these calculation operations, the values $N_{i,j}$ of the photo-multipliers and the coordinates $Xc_{i,j}$ and $YC_{i,j}$ may be stored in a FIFO type system 94 so that they can be used later on.

Contributions to the energy and to the coordinates of the X and Y values of the center of gravity are then grouped. This grouping will be described with reference to FIG. 6 in which the references 80-1, . . . , 80-6 denote 6 column operators of the type described above in relation to FIG. 5.

An accumulator 96 is initialized at the beginning of the sequence and receives input through the BECOL bus, and calculates the sum of the six registers RSEcol1 to RSEcol6 and stores the result in a register 98 (ENERGY). The contents of this register represent the sum of the energy contributions of the 36 photo-multipliers surrounding the presumed position, and therefore the energy of the event.

A second accumulator 100 receives input through the BXCOL bus, and calculates the sum of the six registers RSXcol1 to RSXcol6 and stores the result in a register 102 (RXN). The contents of this register represent $$\sum_i \left[ \sum_j (XC_{ij} * N_{ij}) \right].$$

A third accumulator 104 receives input through the BYCOL bus, and calculates the sum of the six registers RSYcol1 to RSYcol6 and stores the result in a register 106 (RYN). The contents of this register represent $$\sum_i \left[ \sum_j (YC_{ij} * N_{ij}) \right].$$

The RSEcol, RSXcol and RSYcol registers are then released so that they can be used by column operators, and the accumulators are thus once again available to process another event.

Finally, the $X_0$ and $Y_0$ coordinates of the interaction point $P_0$ of the event are calculated by making two divisions using a divider 108:

$X_0 = RXN/\text{ENERGY}$, and $Y_0 = RYN/\text{ENERGY}$, in less than 6 read times so that storage registers 98, 102, 106 can be released. Commercially available integrated pipelined dividers (for example such as the RAYTHEON 3211) are easily capable of achieving these performances and it is even possible to use a single package by making the two divisions in sequence.

Therefore, the position $P_0$ of the event is obtained, and the $X_0$ and $Y_0$ coordinates of this position are stored in a register 110 ($RX_0$ and $RY_0$). At the same time as the divisions, the energy may be pipelined from register 98 to a register 112 in order to release register 98 for the next event.

The $X_0, Y_0$ values obtained provide a particular result with a particular accuracy, which may be unsatisfactory under some circumstances.

However, it was found that the accuracy of the result (in other words the spatial resolution) can be considerably improved if a "weighted" calculation of the center of gravity is added to this calculation. In the following, we will show how this calculation can be implanted in a parallel system compatible with the above, with reference to FIGS. 8 to 13.

In the following, the result obtained using the process described above will be referred to as the unweighted center of gravity, as opposed to the weighted center of gravity.

Once the unweighted center of gravity $P_0$ ($X_0$, $Y_0$) is known, the distance $d_{i,j}$, from the center of each photo-multiplier to $P_0$ can be calculated and the value $N_{i,j}$ can be weighted by calculating a new $N_{i,j}$ called $N'_{i,j}$ such that $N'_{i,j} = K * (N_{i,j})$ where K is a function of $d_{i,j}$.

This function K is determined empirically and is adapted to each type of photo-multiplier and each light collection geometry.

In general, the function K:
 is less than 1 for a small $d_{i,j}$ (to minimize the contribution of the photo-multiplier that receives the event when it is close to its center, is greater than 1 when $d_{i,j}$ is of the same order of magnitude as the size of the photo-multiplier (to increase the contribution of first ring photo-multipliers, in other words photo-multipliers closest to the photo-multiplier that receives the event), tends towards zero when $d_{i,j}$ becomes large (to reduce the contribution of photo-multipliers as the distance increases from the interaction location, since the signal/noise ratio of their contribution deteriorates).

Figure 7A:
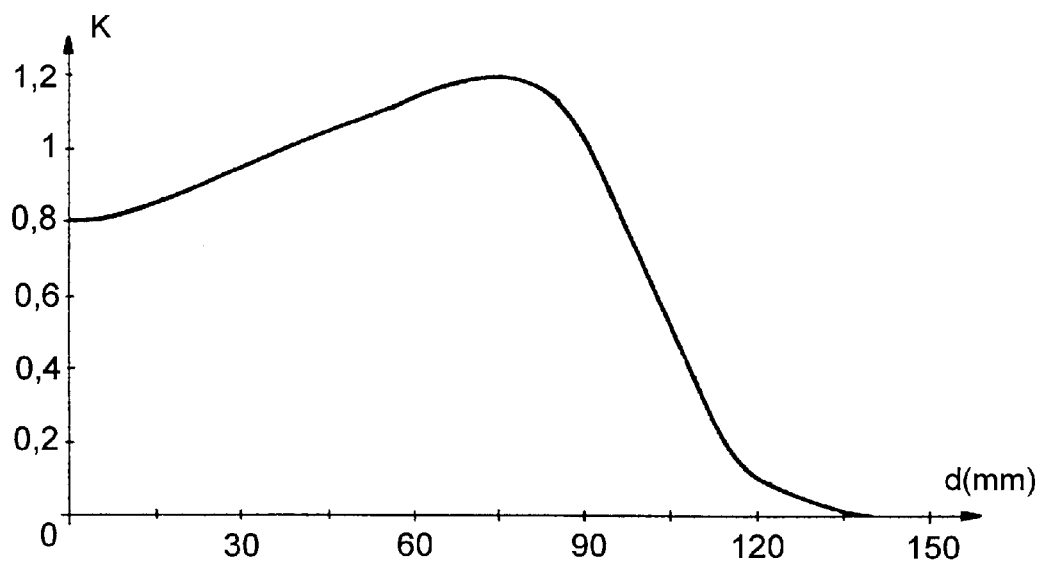
FIGS. 7A and 7B are examples of function K.

FIG. 7A shows a first example of function K(d). This first example is applicable to 75 mm square photo-multipliers. Values of K for particular values of d (with a 5 mm pitch) are given in table I below:

TABLE I

| d  | K     | d   | K     |
|----|-------|-----|-------|
| 0  | 0.8   | 80  | 1.18  |
| 5  | 0.809 | 85  | 1.13  |
| 10 | 0.826 | 90  | 1     |
| 15 | 0.85  | 95  | 0.831 |
| 20 | 0.883 | 100 | 0.663 |
| 25 | 0.916 | 105 | 0.494 |
| 30 | 0.95  | 110 | 0.325 |
| 35 | 0.983 | 115 | 0.117 |
| 40 | 1.016 | 120 | 0.1   |
| 45 | 1.05  | 125 | 0.065 |
| 50 | 1.083 | 130 | 0.035 |
| 55 | 1.116 | 135 | 0.015 |
| 60 | 1.15  | 140 | 0     |
| 65 | 1.176 | 145 | 0     |
| 70 | 1.194 | 150 | 0     |
| 75 | 1.2   | —   | —     |

Figure 7B:
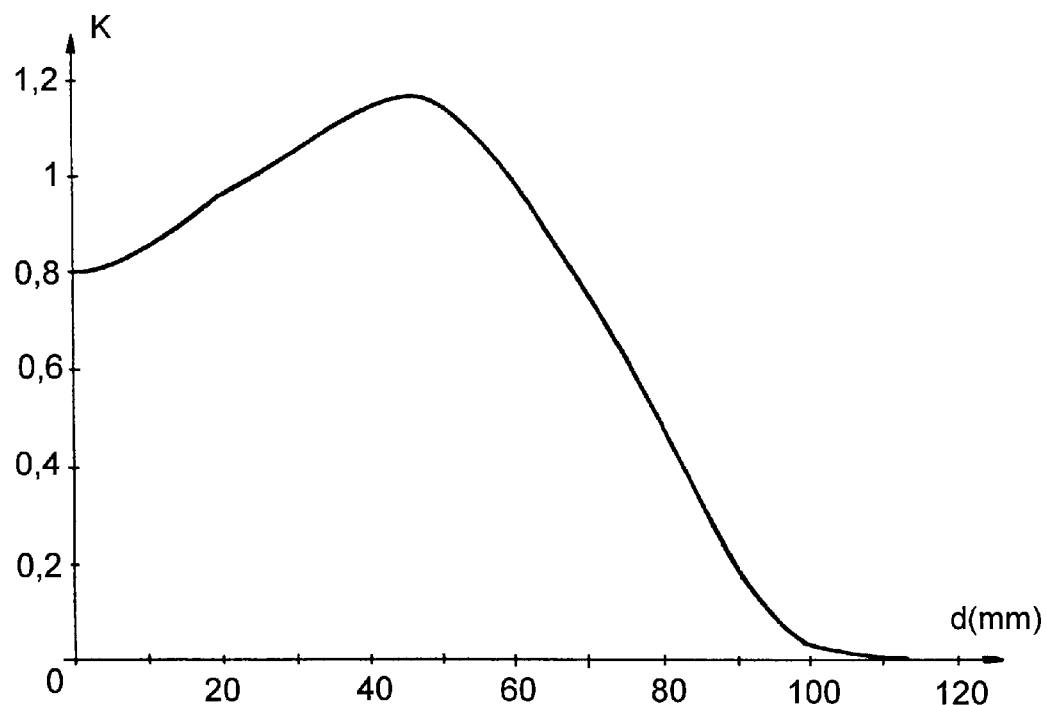

FIG. 7B shows a second example of function K(d). This second example is applicable to 60 mm hexagonal photo-multipliers. Values of K for particular values of d (with a pitch of 5 mm) are given in table II below:

TABLE II

| d  | K     | d   | K     |
|----|-------|-----|-------|
| 0  | 0.8   | 65  | 0.863 |
| 5  | 0.813 | 70  | 0.744 |
| 10 | 0.856 | 75  | 0.619 |
| 15 | 0.906 | 80  | 0.475 |
| 20 | 0.963 | 85  | 0.319 |
| 25 | 1.006 | 90  | 0.181 |
| 30 | 1.056 | 95  | 0.081 |
| 35 | 1.106 | 100 | 0.025 |
| 40 | 1.15  | 105 | 0.013 |
| 45 | 1.169 | 110 | 0     |
| 50 | 1.144 | 115 | 0     |
| 55 | 1.075 | 120 | 0     |
| 60 | 0.975 | —   | —     |

From the implementation point of view, the calculation of the weighted center of gravity is made in the same way as for the unweighted center of gravity, after having replaced $N_{i,j}$ by $N'_{i,j}$. The unweighted center of gravity calculation is followed by a weighting operation using function K, called the weighting function. In the case of the example given above (selecting a set of photo-multipliers defined by 6 rows and 6 columns), this task is carried out by 6 operators, each being capable of processing 6 contributions in 6 read times.

Figure 8:
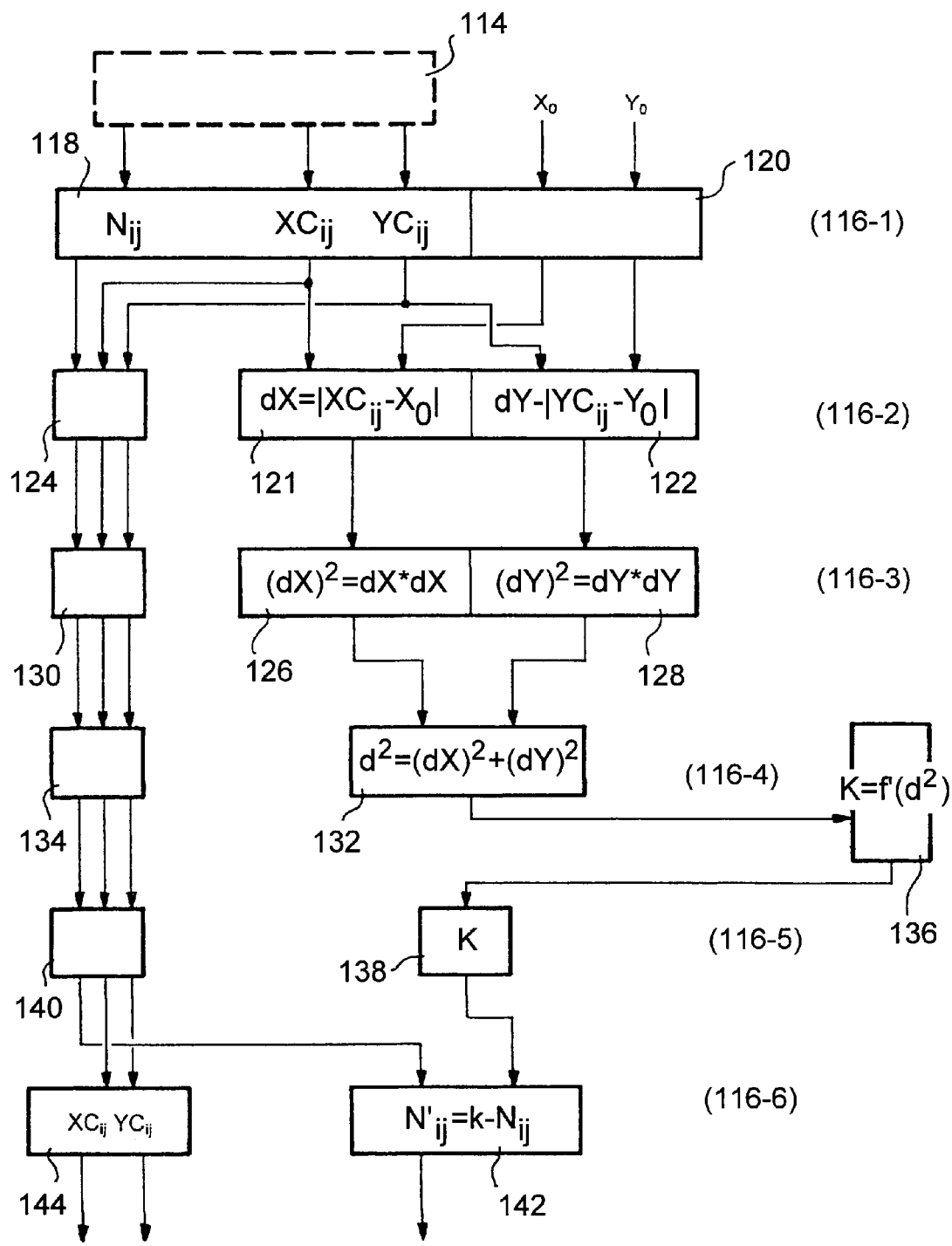
FIG. 8 shows the steps in the calculation of a weighted contribution of each photodetector.

A simple implementation of the weighted center of gravity calculation is shown in FIG. 8.

The values of $N_{i,j}$, $Xc_{i,j}$, $YC_{i,j}$ that were used in the calculation of the unweighted center of gravity have been stored in the FIFO memories denoted globally as reference 114 (the memory 94 (FIG. 5) in which $N_{i,j}$ is stored was already mentioned above). The calculation is organized in steps 116-1, . . . , 116-6 described below, for each weighting operator operating on a column:

116-1: retrieve the first value $N_{i,j}$ and the coordinates of the center of the corresponding photo-multiplier $XC_{i,j}$ and $YC_{i,j}$ (first value written in the FIFO and therefore first value read) and store the weighting operator in an input register 118. At the same time the values $X_0$ and $Y_0$ at the input to the operator are stored in memory 119. This storage operation is not repeated for the next 5 acquisitions of $N_{i,j}$, $XC_{i,j}$ and $YC_{i,j}$, since $P_0$ is unchanged.

116-2: calculate $dX=|XC_{i,j}-X_0|$, and at the same time $dY=|YC_{i,j}-Y_0|$, and store dX, dY, $N_{i,j}$, $XC_{i,j}$ and $YC_{i,j}$ in memories 120, 122, 124. The registers used for step 116-1 are then released, and can then be used to contain values for the next photo-multiplier. The next photo-multiplier is then processed in the same way as the previous photo-multiplier and so on until the sixth.

116-3: calculate $(dX)^2=dX*dX$, and at the same time $(dY)^2=DY*DY$, and store $(dX)^2$, $(dY)^2$, $N_{i,j}$, $XC_{i,j}$, and $YC_{i,j}$ in memories 126, 128, 130. The step 116-2 output registers are then released.

116-4: calculate $d^2=(dX)^2+(dY)^2$ and store $d^2$, $N_{i,j}$, $XC_{i,j}$, and $YC_{i,j}$ in registers 132, 134; the step 116-3 output registers are then released.

116-5: address an EPROM 136 containing the function $K=f'(d^2)$, through the register containing $d^2$. This avoids the need to extract the square root of $d^2$, knowing that it is easy to obtain $K=f'(d^2)$ when $K=f(d)$ is known. K, $N_{i,j}$, $XC_{i,j}$ and $YC_{i,j}$ are then stored in registers 138 and 140, and the step 116-4 output registers are then released.

116-6: calculate $N'_{i,j}=K*N_{i,j}$ and store $N'_{i,j}$, $XC_{i,j}$ and $YC_{i,j}$ in registers 142 and 144; the step 116-5 output registers are then released.

After being broken down ad pipelined in this manner, it is easy to calculate $N'_{i,j}$, since each calculation step is sufficiently simple to be carried out during one read step (typically 100 nsec).

Figure 9:
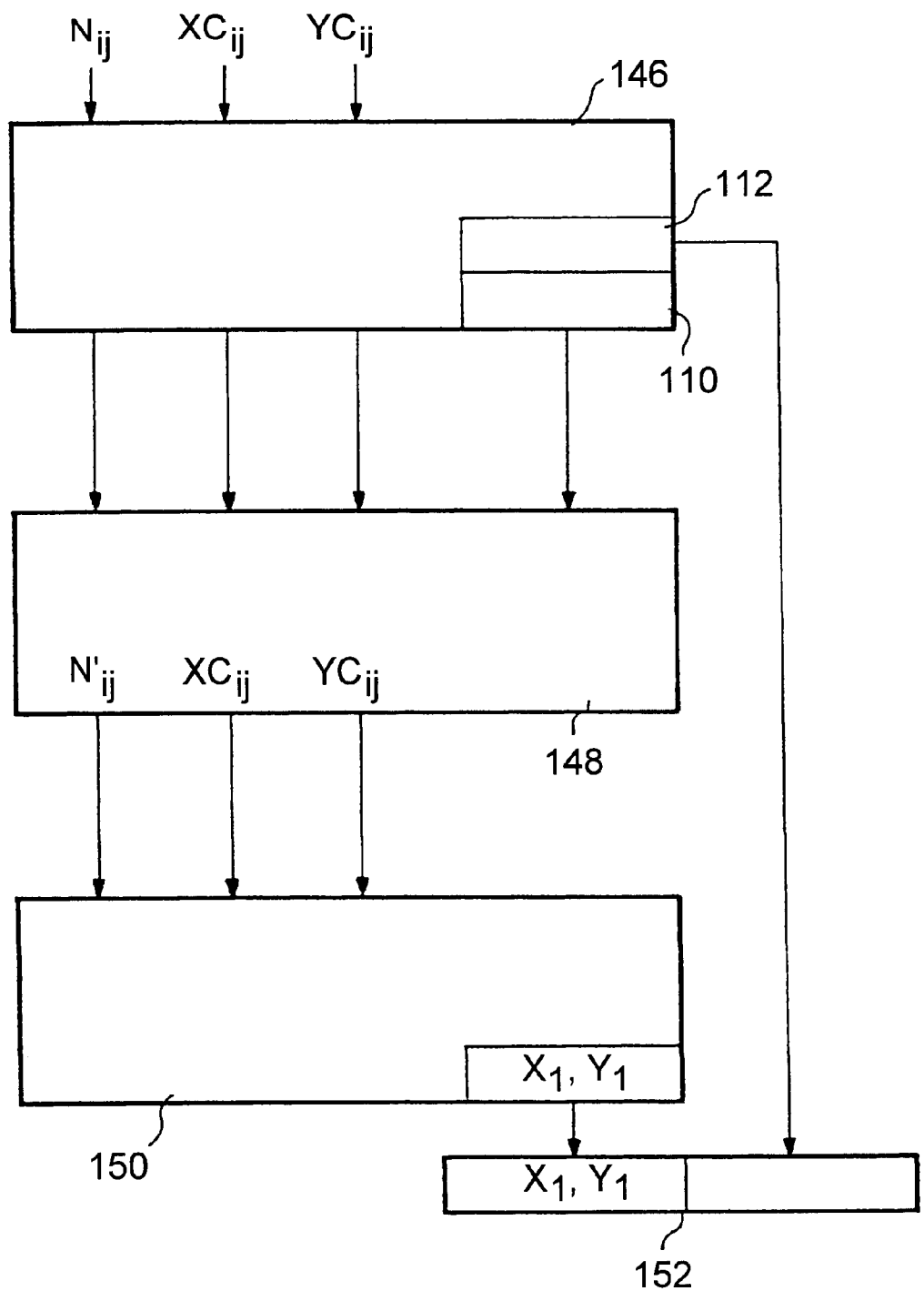
FIG. 9 shows the structure of a calculation system for another embodiment of the invention.

FIG. 9 diagrammatically shows a calculation system according to the invention for implementing the calculation of the unweighted center of gravity, and then the weighted center of gravity. This calculation system comprises:

a first calculation subsystem 146 for calculating the unweighted center of gravity. This first subsystem comprises registers 110 and 112 (see FIG. 6) for storing the calculated values of the energy and the coordinates of the uncorrected position, a second calculation subsystem 148 for calculating the weighting. This second subsystem is of the type described above in relation to FIG. 8, a third calculation subsystem 150 for calculating the weighted center of gravity $X_1$, $Y_1$. This third subsystem has an architecture of the type described in relation to FIGS. 5 and 6.

The output of the weighted center of gravity gives the new coordinates $X_1$, $Y_1$ of the position of the event. The value of the energy can be determined at the same time as the calculations are being carried out; the energy and coordinates of the event are obtained in the final output in the same register 152.

Calculating the weighted center of gravity can improve the position accuracy.

Figure 10:
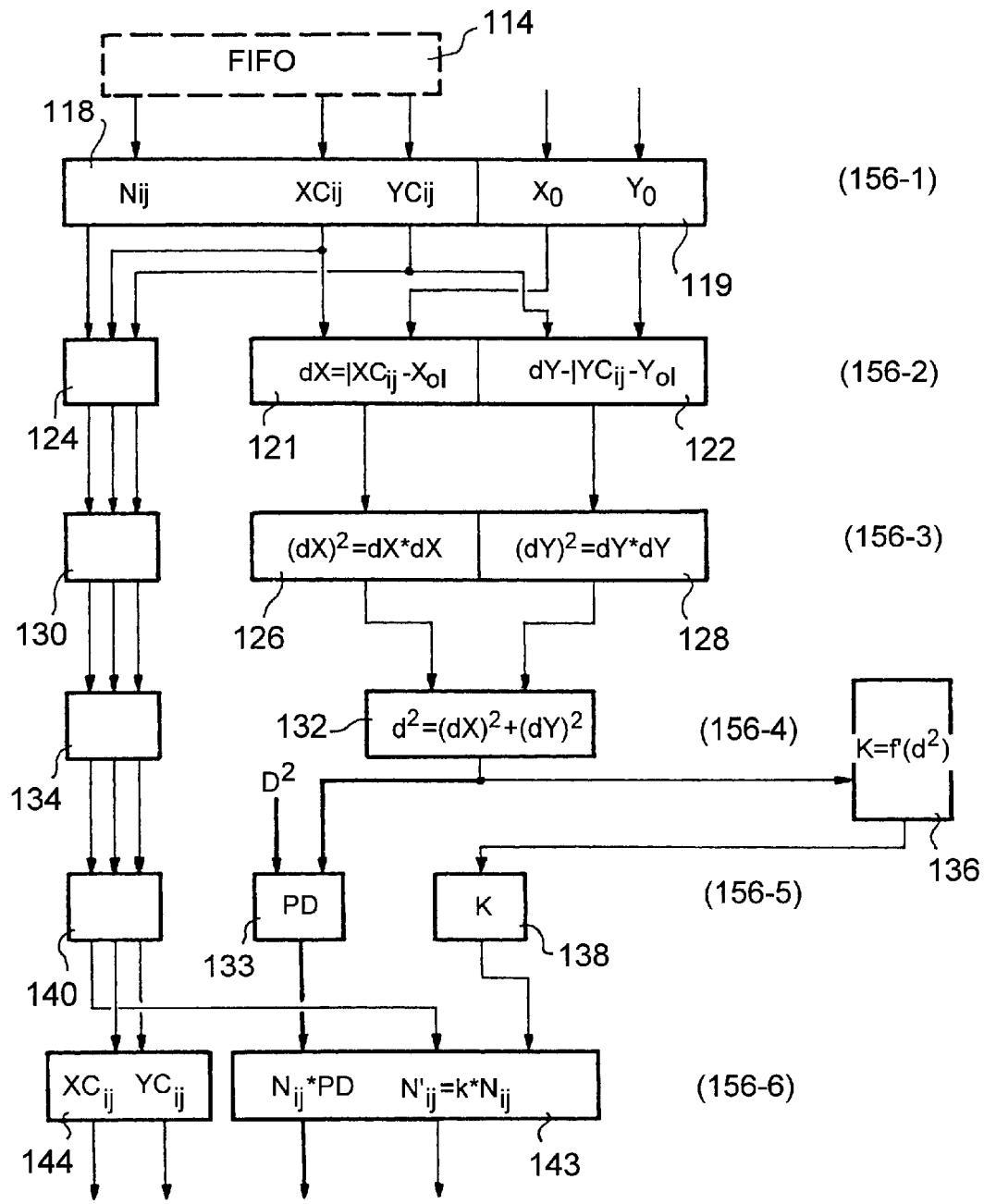
FIG. 10 shows the steps in the calculation of a weighted contribution of each photodetector and for determining photodetectors to be considered in the calculation of the energy.

The accuracy of the energy calculation can also be improved if it is calculated using only the photo-multipliers that are at a distance less than a determined value from $P_0$. In this way, the photo-multipliers which make a contribution composed essentially of noise, among the $N_1$ photo-multipliers, can be eliminated. It will be noted that the number of these photo-multipliers is greater when the position $P_0$ is close to the edges of the photo-multipliers field. FIG. 10 shows an implementation of the calculation of the weighted center of gravity and the filtered energy.

References in this figure identical to the references in FIG. 8 denote identical or corresponding elements.

Steps 156-1, 156-2, 156-3, 156-4 are identical to steps 116-1, 116-2, 116-3, 116-4. Furthermore, during step 156-5, $d^2$ is compared with a value $D^2$ where D is the distance from the interaction point $P_0$ beyond which it is considered that the signal/noise ratio of the contribution of a photo-multiplier is too low. The result of the comparison, called PD, is equal to the following values: PD=0 if $d^2>D^2$ and PD=1 if $d^2 \leq D^2$. This result is stored in a register 133.

During step 156-6, the value $N'_{i,j} *PD$ (actually 0 when $d^2>D^2$ and Ni,j when $d^2 \leq D^2$) is stored in a register 143 in addition to the values $N'_{i,j}$, $XC_{i,j}$ and $YC_{i,j}$.

Figure 11:
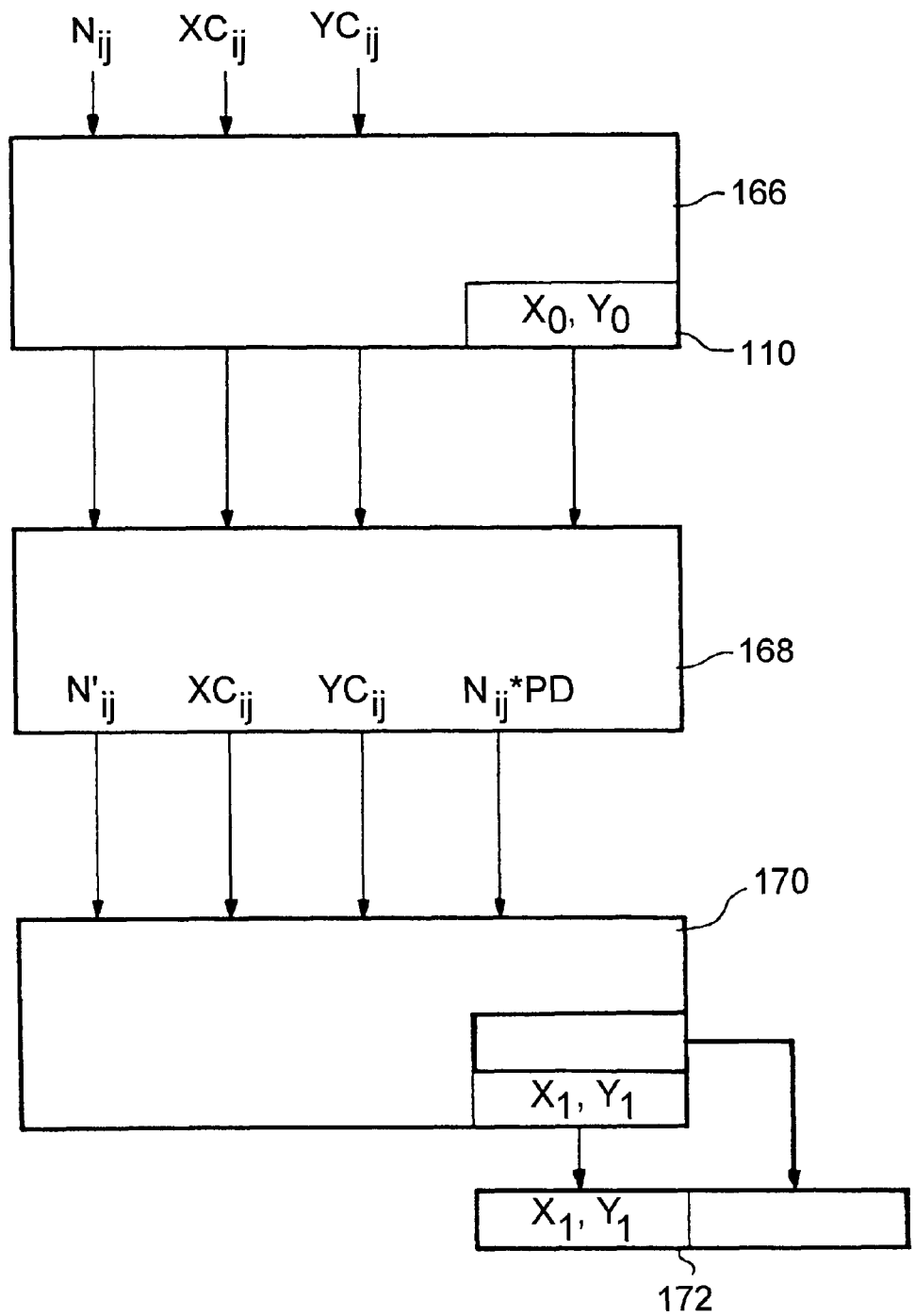
FIG. 11 shows the structure of a calculation system for another embodiment of the invention.

FIG. 11 diagrammatically shows a calculation system according to the invention for implementation of the calculation of the unweighted center of gravity, and then the weighted center of gravity. This calculation system comprises:

- a first calculation subsystem 166 for calculating the unweighted center of gravity. This first subsystem is similar to subsystem 146 shown in FIG. 9. It comprises register 110 (see FIG. 6) for storing calculated values of the coordinates of the uncorrected position,
- a second calculation subsystem 168 for calculating the weighting. This second subsystem is of the type described above in relation to FIG. 10. It calculates $N'_{i,j}$, $XC_{i,j}$, $YC_{i,j}$ and also $N_{i,j} *PD$,
- a third calculation subsystem 170 for calculating the weighted center of gravity $X_1$, $Y_1$ and the new value of the energy. The architecture of this third subsystem will be described below in relation to FIGS. 12 and 13.

Figure 12:
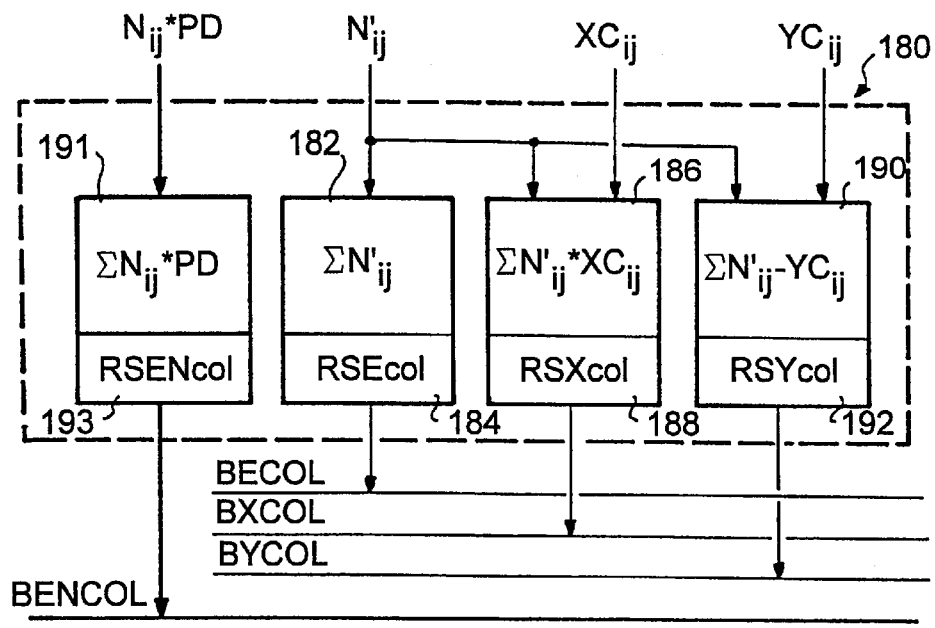
FIG. 12 shows the structure of a column operator for another embodiment of the invention.

FIG. 12 represents a column operator 180. In addition to the values $N_{i,j}$ and $N_{i,j} *PD$ of the column photo-multipliers, the coordinates $XC_{i,j}$ and $YC_{i,j}$ of the centers of the corresponding photo-multipliers output by the calculation subsystem 168, are input into this column operator.

Each column operator 180 performs four operations, preferably in parallel.

A first operation consists of calculating the contribution of the column to the energy. For example, after being initialized at the beginning of the sequence, an accumulator 191 takes the sum of the values $N_{i,j} *PD$ of the 6 photo-multipliers in the column and stores the result in a register 193 (RSENcol). The outputs from the six registers (RSENcol1 to RSENcol6) are grouped on a common bus BENCOL.

A second operation consists of calculating the sum $\Sigma N'_{i,j}$ for the corresponding column. For example, after being initialized at the beginning of the sequence, an accumulator 182 takes the sum $\Sigma N'_{i,j}$ for the 6 photo-multipliers in the column, and stores the result in a register 184.

A third operation consists of calculating the contribution of the column to the X value of the center of gravity. For example, after being initialized at the beginning of the sequence, a multiplier-accumulator 186 takes the sum of the contributions to the X value of the center of gravity of the 6 photo-multipliers in the column, and stores the result in a register 188 (RSXcol). The outputs from the six registers (RSXcol1 to RSXcol6) are grouped on a common bus BXCOL.

A fourth operation consists of calculating the contribution of the column to the Y value of the center of gravity. For example, after being initialized, a second multiplier-accumulator 190 takes the sum of the contributions to the Y value of the center of gravity of the 6 photo-multipliers in the column, and stores the result in a register 192 (RSYcol). The outputs from the six registers (RSYcol1 to RSYcol6) are grouped on a common bus BYCOL.

At the end of the 6 read times, the 6 column operators that have completed their work become available for another read since the results of the first read are stored.

Contributions to the energy and to the coordinates of the X and Y values of the center of gravity are then grouped. This grouping will be described with reference to FIG. 13 in which the references 180-1, ..., 180-6 denote 6 column operators of the type described above in relation to FIG. 12.

An accumulator 195 is initialized at the beginning of the sequence and receives input through the BENCOL bus, and calculates the sum of the six registers RSENcol1 to RSENcol6 and stores the result in a register 197 (ENERGY). The contents of this register represent the sum of the corrected contributions $N_{i,j} *PD$ of the 36 photo-multipliers surrounding the presumed position, and therefore the energy of the event.

A second accumulator 196 is initialized at the beginning of the sequence and receives input through the BECOL bus, and calculates the sum of the six registers RSEcol1 to RSEcol6 and stores the result in a register 198.

A third accumulator 200 receives input through the BXCOL bus, and calculates the sum of the six registers RSXcol1 to RSXcol6 and stores the result in a register 202 (RXN). The contents of this register represent $$\sum_i \left[ \sum_j (XC_{ij} * N'_{ij}) \right].$$

A fourth accumulator 204 receives input through the BYCOL bus, and calculates the sum of the six registers RSYcol1 to RSYcol6 and stores the result in a register 206 (RYN). The contents of this register represent $$\sum_i \left[ \sum_j (YC_{ij} * N'_{ij}) \right].$$

The RSEcol, RSXcol and RSYcol registers are then released so that they can be used by column operators, and the accumulators are thus once again available to process another event.

Finally, the $RX_1$ and $RY_1$ coordinates of the interaction point of the event are calculated by making two divisions using a divider 208:

$$RX_1 = RXN/\Sigma N'_{i,j}, \text{ and}$$

$$RY_1 = RYN/\Sigma N'_{i,j},$$

in less than 6 read times so that storage registers 198, 202, 206 can be released. Commercially available integrated pipelined dividers (for example such as the RAYTHEON 3211) are easily capable of achieving these performances and it is even possible to use a single package by making the two divisions in sequence.

Therefore, the position of the event is obtained, and the $RX_1$ and $RY_1$ coordinates of this position are stored in a register 210 ($RX_1$ and $RY_1$). At the same time as the divisions, the energy may be pipelined from register 197 to a register 212 in order to release register 197 for the next event.

Therefore registers 210 and 212 contain the values of the corrected coordinates and the value of the corrected energy of the event.

Although the general version of the system according to the invention described above requires a large amount of electronics, it is still very competitive compared with systems using programmable calculation means (microprocessors or DSP). Particularly because in some configurations, its construction may be considerably simplified. For example, this is the case for a gamma-camera head composed of square photo-multipliers in which it is assumed that the centers of the photo-multipliers are on a regular and square mesh. In this case the concept of a pitch can be used (distance in X and Y between the centers of two contiguous photo-multipliers) which simplifies most operators.

We will now describe how the signal output from each photo-multiplier is detected and processed, and in particular how a presumed position of the event can be calculated.

Figure 14:
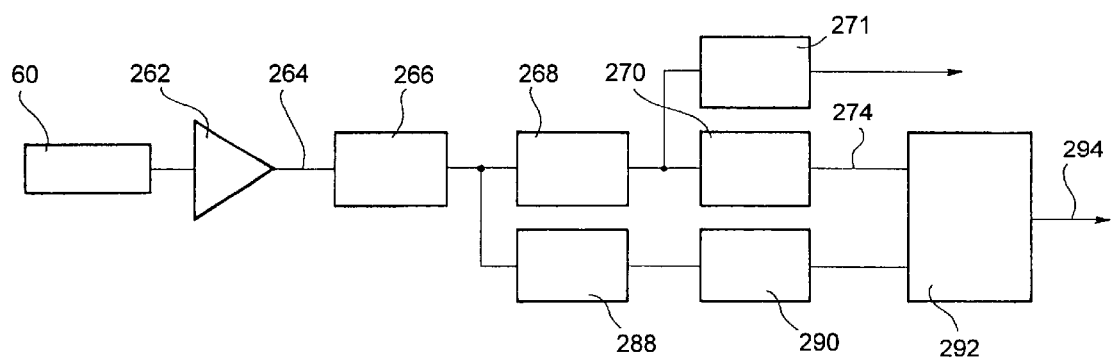
FIG. 14 shows a circuit associated with the photodetector for processing of data from this photodetector.

FIG. 14 shows part of the device associated with a single photo-multiplier 60. The photo-multiplier 60 is connected to a current-voltage converter 262. In response to an event detected by the photo-multiplier, a signal is obtained on the output 264 from the current-voltage converter 262, for example of the type illustrated in FIG. 15A.

Figure 15A:
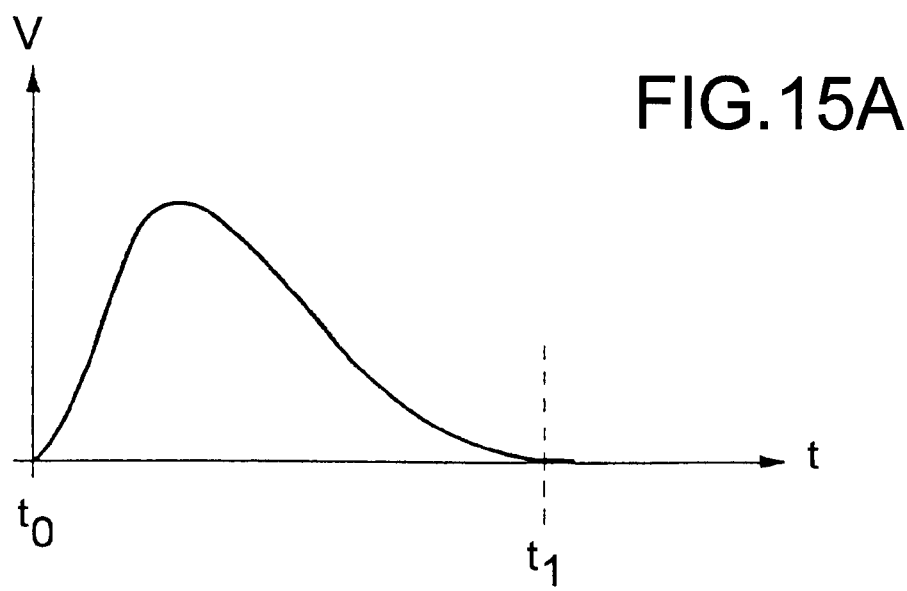
FIGS. 15A and 15B show an analog signal output by a photodetector (FIG. 15A), and the corresponding digitized analog signal (FIG. 15B)

The ordinate of the graph in FIG. 15A shows the amplitude of the signal corresponding to the pulse, and the abscissa shows the time. The amplitude of the signal and the time are indicated in an arbitrary scale. $t_0$ denotes the start time of the pulse output by the photodetector and $t_1$ denotes the time at which the pulse drops to almost zero, after having passed through a maximum. For guidance, the duration corresponding to the interval $t_1$–$t_0$ is of the order of one microsecond, in the case of a photo-multiplier of a gamma-camera coupled to an NaI(Tl) crystal.

Figure 15B:
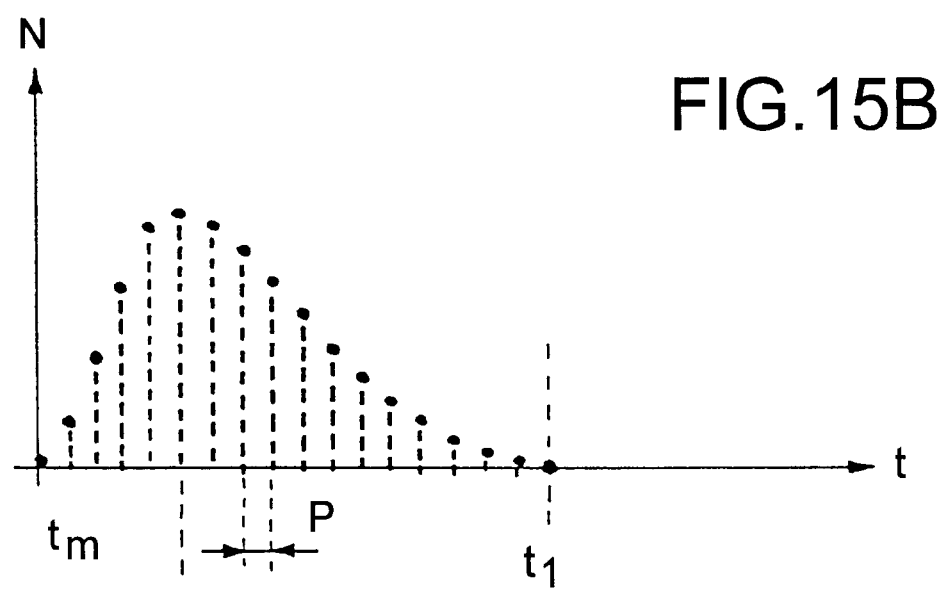

The analog signal present on the output terminal 264 is directed to an analog-digital converter 266. This converter samples each signal pulse taking a number of samples n as shown in FIG. 15B. Two consecutive samples are separated by a step or clock interval p (the clock operates at 1/p Hz).

For example, the converter samples each signal pulse using n=10 samples. Thus for a 1 microsecond signal, a sample is taken every 100 nanoseconds.

The analog-digital converter 266 is preferably a fast converter of the "flash" type capable of operating at a frequency of the order of 10 to 20 Megahertz.

The digital signal output from the analog-digital converter 266 is directed towards a digital adder 268. This adder takes the sliding sum of the samples sent to it by the analog-digital converter 266. The sliding sum is carried out on a given number of samples. For example, this predetermined number may be equal to 10.

For each photodetector i,j, this sliding sum, or the digital integral of the signal output in response to an event, corresponds to the magnitude $N_{i,j}$, already introduced above.

At the same time, the result of the summation made with means 268 is stored in a register 271. The storage function may be composed of several registers so that several events at very close time intervals can be stored.

The value of the sliding sum is directed towards comparison means 270. These means compare the value of the sliding sum with a predetermined fixed threshold value at an input 272 of comparator 270. This comparator sends a binary signal to output 274 representing the result of the comparison (for example 0 if the value of the sliding sum is less than the fixed reference value, and 1 if the value of the sliding sum is greater than the reference value).

In order to limit the duration of this overshoot, it will only be validated during a time window centered on the maximum of the sliding sum. This separates events that are close in time, but are geographically distinct on the detector field.

This window is positioned by using the time at which the encoded signal passes through a maximum, as a reference. This detection is made by means 288 by comparing the current value of the encoder output with the previous value. When the current value is less than the previous value, the comparator 288 outputs a pulse. This pulse is sent to an offset register 290, in which the delay $n_1$ is adjusted to generate a time window centered on the maximum of the sliding sum. To take account of the inaccuracy (approximately one sampling step) with which the maximum position of the encoded signal is determined, the time window will be activated during $n_0$ sampling steps, where $n_0 \geq 3$ (for example $n_0=3$), this choice of a minimum of three minimizing simultaneous signals exceeding the threshold between photo-multipliers activated by the same event.

The signal obtained at the output from comparator 270 and the output signal from the offset register 290 are applied as inputs to an AND gate 292, which produces a threshold overshoot signal on its output 294 at the required instant with respect to the digital signal passing through a maximum.

Figure 16:
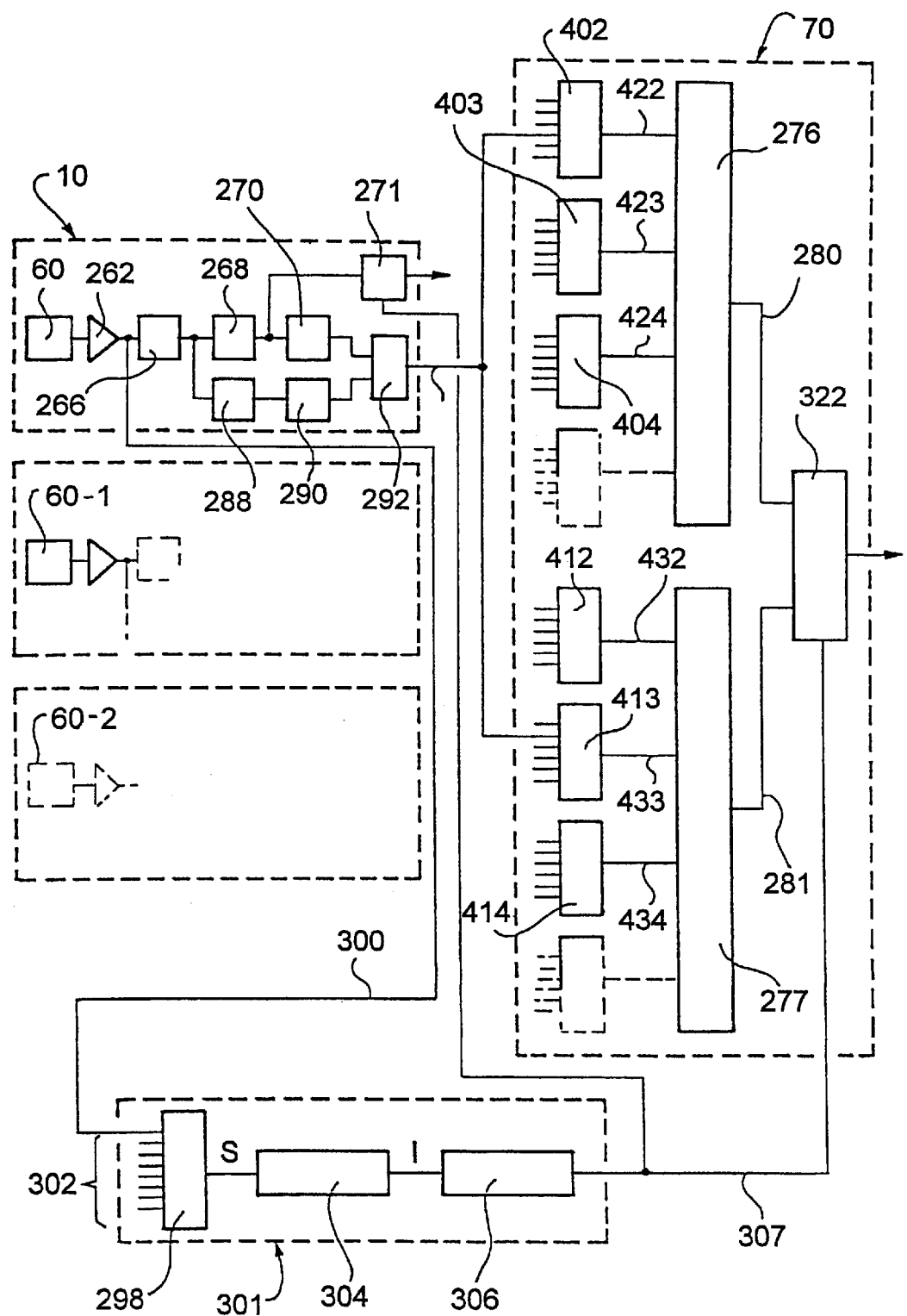
FIG. 16 shows an embodiment of a device for determining a presumed position of an event.

FIG. 16 shows a device according to the invention for processing signals output from several photodetectors 60, 60-1, 60-2. In this figure, references identical to the references in FIG. 10 denote similar or corresponding elements.

In this figure, it can be seen that an analog signal 300 of the type described above with relation to FIG. 15A can be taken from the output of the current-voltage converter 262. In FIG. 16, reference 302 globally denotes all analog signals taken from other current-voltage converters 262-1, 262-2, etc. All these signals are input into an analog adder 298 that outputs a signal S which is the sum of all analog signals output by a given number of photodetectors, for example by all photodetectors. A device 304 outputs a pulse I when the signal S passes through its maximum. For example, this device 304 comprises a differentiator (capacitor, amplifier and resistances between the amplifier input and output); the output from this differentiator is input into a comparator that detects when the differentiator output changes to 0. Pulse I is input into an offset register 306 that uses a step p that is controlled by clock H. The output 307 from this register is called a storage pulse and in particular triggers the storage register 271 corresponding to photodetector 60. It also triggers each storage register associated with each photodetector. The delay in the offset register 306 is adjusted so that the rising front of the storage signal 307 is synchronous with the moment at which the sums must be stored in registers 271.

For example, the set of photodetectors 60, 60-1,
60-2, . . . may be distributed in a two-dimensional network.

In order to mark the presumed position (or the uncorrected position) of an event with respect to this two-dimensional photodetectors network, it is advantageous to associate a read access memory with a first coordinate direction in the photodetectors network, and a read access memory with a second coordinate direction in the photodetectors network. If this network is identified by rows and columns, one read access memory can thus be associated to identify a "row" coordinate, and one read access memory can be used to identify a "column" coordinate.

More precisely, in a device according to the invention of the type illustrated in FIG. 6, the outputs 294 that represent photodetectors at the center of the interaction (when the outputs are active) are used as follows:

an OR circuit (402) contains type 294 outputs from the photodetectors in a single column and generates an active signal 422 when at least one of its inputs is active. There is one 402 type circuit for each column, an OR circuit (412) contains type 294 outputs from the photodetectors in a single row and generates an active signal 432 when at least one of its inputs is active. There is one 412 type circuit for each row.

Type 422 signals are the addresses of a PROM 276 that is programmed to output the coordinate (280) of the presumed position with respect to the columns. Similarly, type 432 signals are the addresses of a second PROM 277 that is programmed to output the coordinate (281) of the presumed position with respect to the rows. The presumed position represented by the pair of values (280, 281) is stored in a register 322, at the same time as the contributions of all photodetectors are stored in their corresponding registers (271). This storage operation is triggered by the signal 307 generated by register 306.

What is claimed is:

1. Process for determining the position $P_0$ ($X_0$, $Y_0$) of an event in an X, Y coordinate system making use of a set of N photodetectors laid out in matrix form in rows and columns, an arbitrary detector in a column with rank i and a row with rank j being identifiable in the coordinate system, the event inducing a signal in the N photodetectors, comprising sampling, further comprising digitization of the signals output by each photodetector, and a summation of the digitized samples:

a) a step in which the sliding sum of the digitized samples is stored, the current sum being stored each time that samples are added, the final sum representing the energy $N_{i,j}$ output by the sensor for each photodetector in a column of rank i and a row of rank j;

b) a step in which the following are determined for each column of rank i:
the contribution of the column to total energy induced by the event in the set of photodetectors,
the contribution of the column to the X value of the center of gravity of the event,
the contribution of the column to the Y value of the center of gravity of the event, c) a step in which the following are determined:
the total energy induced by the event in the set of photodetectors, by summation of the contributions of each column calculated in step b,
the coordinates of the center of gravity ($X_O$, $Y_O$) of the event with respect to the N photodetectors.

2. Process according to claim 1 comprising a preliminary step for detection of a presumed position of an event.

3. Process according to claim 2, also comprising a step for the delimitation of a sub-set of $N_1$ photodetectors among the set of N photodetectors around the presumed position of the event, only the signals from the $N_1$ photodetectors of this sub-set being processed according to steps b) and c).

4. Process according to claim 3, also comprising the following steps after the coordinates of the center of gravity ($X_O$, $Y_O$) of the event with respect to the N photodetectors have been determined:

d) determine a distance $d_{i,j}$ between $P_O$ and each of the photodetectors for which the signals are used in steps b) and c);

e) weight the signal $N_{i,j}$ output by each photodetector, for which the signals are used in steps b) and c) to obtain a weighted signal value $N'_{i,j}=K*N_{i,j}$ where K is a function of $d_{i,j}$.

5. Process according to claim 4, the function K being:
less than 1 if $d_{i,j}$ is less than the size of the photodetector;
greater than 1 if $d_{i,j}$ is greater than or is of the same order of magnitude as the size of the photodetector such that the weighted signal value accounts for a contribution of a photodetector having the distance $d_{i,j}$ between the $P_o$ and the photodetector;
approximately equal to 0 if $d_{i,j}$ becomes large such that a signal/noise ratio of the contribution of the photodetector deteriorates due to the distance between the $P_o$ and the photodetector.

6. Process according to claim 5, also comprising:

b') a step in which the following are determined using the values of the weighted signal, $N'_{i,j}$, for each column i:
the contribution of the column to the total energy induced by the event in the set of photodetectors;
the contribution of the column to the X value of the center of gravity of the event;
the contribution of the column to the Y value of the center of gravity of the event;

c') a step in which the following are determined using the values of the weighted signal, $N'_{i,j}$:
the total energy induced by the event in the set of photodetectors;
the new coordinates of the center of gravity ($X'_O$, $Y'_O$) of the event with respect to the N photodetectors.

7. Process according to claim 4, also comprising:

b') a step in which the following are determined using the values of the weighted signal, $N'_{i,j}$, for each column i:
the contribution of the column to the total energy induced by the event in the set of photodetectors,
the contribution of the column to the X value of the center of gravity of the event,
the contribution of the column to the Y value of the center of gravity of the event c') a step in which the following are determined using the values of the weighted signal, $N'_{i,j}$:
the total energy induced by the event in the set of photodetectors,
the new coordinates of the center of gravity ($X'_O$, $Y'_O$) of the event with respect to the N photodetectors.

8. Process according to claim 3, also comprising the following steps after the coordinates of the center of gravity $P_O$ ($X_O$, $Y_O$) of the event with respect to the N photodetectors have been determined:

d') determine a distance $d_{i,j}$ between $P_O$ and each photodetector for which the signals are used in steps b) and c);

f) compare with a value D, for each value of $d_{i,j}$;

g) determine values $N_{i,j}$ *PD, where PD=0 if $d_{i,j}$>D and PD≠0 if $d_{i,j}$≦D for each photodetector.

9. Process according to claim 8, also comprising a step h) to determine a new value of the total energy as a function of the values $N_{i,j}$ *PD.

10. Process according to claim 9, the new value of the energy according to step h) being determined in the following steps:

b") determine the contribution of each column to the total energy induced by the event in the set of photodetectors, as a function of the values $N_{i,j}$ *PD;

c") determine the total energy induced by the event in the set of photodetectors by taking a sum of the contributions obtained in b") for the various columns.

11. Process according to claim 2, also comprising the following steps after the coordinates of the center of gravity ($X_O$, $Y_O$) of the event with respect to the N photodetectors have been determined:

d) determine a distance $d_{i,j}$ between $P_O$ and each of the photodetectors for which the signals are used in steps b) and c);

e) weight the signal $N_{i,j}$ output by each photodetector, for which the signals are used in steps b) and c) to obtain a weighted signal value $N'_{i,j}=K*N_{i,j}$ where K is a function of $d_{i,j}$.

12. Process according to claim 11, the function K being:

less than 1 if $d_{i,j}$ is less than the size of the photodetector;

greater than 1 if $d_{i,j}$ is greater than or of the same order of magnitude as the size of the photodetector such that the weighted signal value accounts for a contribution of a photodetector having the distance $d_{i,j}$ between the $P_o$ and the photodetector;

approximately equal to 0 if $d_{i,j}$ becomes large such that a signal/noise ratio of the contribution of the photodetector deteriorates due to the distance between the $P_o$ and the photodetector.

13. Process according to claim 12, also comprising:

b') a step in which the following are determined using the values of the weighted signal, $N'_{i,j}$, for each column i:
the contribution of the column to the total energy induced by the event in the set of photodetectors;
the contribution of the column to the X value of the center of gravity of the event;
the contribution of the column to the Y value of the center of gravity of the event;

c') a step in which the following are determined using the values of the weighted signal, $N'_{i,j}$:
the total energy induced by the event in the set of photodetectors;
the new coordinates of the center of gravity ($X'_O$, $Y'_O$) of the event with respect to the N photodetectors.

14. Process according to claim 11, also comprising:

b') a step in which the following are determined using the values of the weighted signal, $N'_{i,j}$, for each column i:
the contribution of the column to the total energy induced by the event in the set of photodetectors,
the contribution of the column to the X value of the center of gravity of the event,
the contribution of the column to the Y value of the center of gravity of the event, c') a step in which the following are determined using the values of the weighted signal, $N'_{i,j}$:
the total energy induced by the event in the set of photodetectors,
the new coordinates of the center of gravity ($X'_O$, $Y'_O$) of the event with respect to the N photodetectors.

15. Process according to claim 2, also comprising the following steps after the coordinates of the center of gravity $P_O$ ($X_O$, $Y_O$) of the event with respect to the photodetectors have been determined:

d') determine a distance $d_{i,j}$ between $P_O$ and each photodetector for which the signals are used in steps b) and c);

f) compare with a value D, for each value of $d_{i,j}$;

g) determine a value $N_{i,j}$ *PD, where PD=O if $d_{i,j}$>D and PD≠O if $d_{i,j}$≦D for each photodetector.

16. Process according to claim 15, also comprising a step h) to determine a new value of the total energy as a function of the values $N_{i,j}$ *PD.

17. Process according to claim 16, the new value of the energy according to step h) being determined in the following steps:

b") determine the contribution of each column to the total energy induced by the event in the set of photodetectors, as a function of the values $N_{i,j}$ *PD;

c") determine the total energy induced by the event in the set of photodetectors by taking a sum of the contributions obtained in b") for the various columns.

18. Process according to claim 1, also comprising the following steps after the coordinates of the center of gravity ($X_0$, $Y_0$) of the event have been determined with respect to the N photodetectors:

determine a distance $d_{i,j}$ between $P_o$ and each of the photodetectors for which the signals are used in steps b) and c);

e) weight the signal $N_{i,j}$ output by each photodetector, for which the signals are used in steps b) and c) to obtain a weighted signal value $N'_{i,j}=K*N_{i,j}$ where K is a function of $d_{i,j}$.

19. Process according to claim 18, the function K being:

less than 1 if $d_{i,j}$ is less than the size of the photodetector;

greater than 1 if $d_{i,j}$ is greater than or of the same order of magnitude as the size of the photodetector such that the weighted signal value accounts for a contribution of the photodetector having the distance $d_{i,j}$ between the $P_o$ and the photodetector;

approximately equal to 0 if $d_{i,j}$ becomes large such that a signal/noise ratio of the contribution of the photodetector deteriorates due to the distance $d_{i,j}$ between the $P_o$ and the photodetector.

20. Process according to claim 19, also comprising:

b') a step in which the following are determined using the values of the weighted signal, $N'_{i,j}$, for each column i:
the contribution of the column to the total energy induced by the event in the set of photodetectors;
the contribution of the column to the X value of the center of gravity of the event;
the contribution of the column to the Y value of the center of gravity of the event;

c') a step in which the following are determined using the values of the weighted signal, $N'_{i,j}$;
the total energy induced by the event in the set of photodetectors;
the new coordinates of the center of gravity ($X'_O$, $Y'_O$) of the event with respect to the N photodetectors.

21. Process according to claim 18, also comprising:

b') a step in which the following are determined using the values of the weighted signal, $N'_{i,j}$, for each column i:
the contribution of the column to the total energy induced by the event in the set of photodetectors,
the contribution of the column to the X value of the center of gravity of the event,
the contribution of the column to the Y value of the center of gravity of the event, c') a step in which the following are determined using the values of the weighted signal, $N'_{i,j}$:
the total energy induced by the event in the set of photodetectors,
the new coordinates of the center of gravity ($X'_O$, $Y'_O$) of the event with respect to the N photodetectors.

22. Process according to claim 1, also comprising the following steps after the coordinates of the center of gravity $P_O(X_O, Y_O)$ of the event with respect to the N photodetectors have been determined:

d') determine a distance $d_{i,j}$ between $P_O$ and each photodetector for which the signals are used in steps b) and c);

f) compare with a value D, for each value of $d_{i,j}$;

g) determine a value $N_{i,j}$ *PD, where PD=0 if $d_{i,j}$>D and PD≠0 if $d_{i,j}$≦D for each photodetector.

23. Process according to claim 22, also comprising a step
h) to determine a new value of the total energy as a function of the values $N_{i,j}$ *PD.

24. Process according to claim 23, the new value of the energy according to step h) being determined in the following steps:

b") determine the contribution of each column to the total energy induced by the event in the set of photodetectors, as a function of the values $N_{i,j}$ *PD;

c") determine the total energy induced by the event in the set of photodetectors by taking a sum of the contributions obtained in b") for the various columns.

25. Process according to claim 1, the photodetectors being photo-multipliers of a gamma-camera.

26. Process according to claim 25, wherein the process is an imagery process in correction of transmission attennation.

27. Process according to claim 25, wherein the process is a PET coincidence imagery process.

28. Device for determining the position $P_0$ of an event with respect to a set i of N photodetectors arranged in columns i, this event inducing a signal in the N photodetectors, comprising means (266, 268) of digitizing a signal output by each photodetector (60), and of calculating a value $N_{i,j}$ representing the energy of the signal output by each photodetector, characterized in that it also comprises:

a) means (82, 86, 90) of determining, for each column i:
the contribution of the column to the total energy induced by the event in the set of photodetectors;
the contribution of the column to a X value of a center of gravity of the event;
the contribution of the column to a Y value of a center of gravity of the event;

b) means (96, 100, 104, 108) of determining:
the total energy induced by the event in the set of photodetectors;
the coordinates of a center of gravity $(X_0, Y_0)$ of the event with respect to the N photodetectors.

29. Device according to claim 28, comprising means (70) of detecting the presumed position of an event.

30. Device according to claim 29, also comprising means (68, 74) of delimiting a subset of $N_1$ photodetectors among the set of N photodetectors around a presumed position of the event.

31. Device according to claim 28, also comprising means (148) of:

d) determining a distance $d_{i,j}$ between $P_O$ and each photodetector for which the signals are used to calculate the energy and the center of gravity;

e) weighting the value $N_{i,j}$ output by each photodetector for which the signals are used to calculate the energy and the center of gravity to obtain a weighted signal value $N'_{i,j}$=K*$N_{i,j}$ where K is a function of $d_{i,j}$.

32. Device according to claim 31, in which the function K is:

less than 1 if $d_{i,j}$ is less than the size of the photodetector;

greater than 1 if $d_{i,j}$ is greater than or of the same order of magnitude as the size of the photodetector such that the weighted signal value accounts for a contribution of a photodetector having the distance $d_{i,j}$ between the $P_o$ and the photodetector;

approximately equal to 0 if $d_{i,j}$ becomes large such that a signal/noise ratio of the contribution of the photodetector deteriorates due to the distance between the $P_o$ and the photodetector.

33. Device according to claim 32, also comprising means (150) for:

b') determining the following for each column i making use of the values of the weighted signal $N'_{i,j}$:
the contribution of the column to total energy induced by the event in the set of photodetectors;
the contribution of the column to the X value of the center of gravity of the event;
the contribution of the column to the Y value of the center of gravity of the event;

c') determining the following making use of the values of the contributions obtained in b'):
the total energy induced by the event in the set of photodetectors;
the new coordinates of the center of gravity $(X_1, Y_1)$ of the event with respect to the N photodetectors.

34. Device according to claim 28, also comprising means of:

d') determining a distance $d_{i,j}$ between $P_O$ and each photodetector, for which the signals are used to calculate the center of gravity and the energy;

f) comparing each value of $d_{i,j}$ with a value D;

g) determining values $N_{i,j}$ *PD, where PD=0 if $d_{i,j}$>D and PD=0 if $d_{i,j}$≦D for each photodetector for which the signals are used to calculate the center of gravity and the energy.

35. Device according to claim 34, also comprising means of determining a new value of the total energy as a function of the values $N_{i,j}$ *PD.

36. Device according to claim 35, the means of determining a new value of the energy comprising:

means (191) of determining the contribution of each column to the total energy induced by the event in the set of photodetectors as a function of the values $N_{i,j}$ *PD;

means (195) of determining the total energy induced by the event in the set of photodetectors.

37. Device according to claim 28, the photodetectors being photo-multipliers in a gamma-camera.

* * * * *